(12) United States Patent
Scher et al.

(10) Patent No.: US 7,912,653 B1
(45) Date of Patent: *Mar. 22, 2011

(54) NANOCRYSTAL TAGGANTS

(75) Inventors: Erik C. Scher, San Francisco, CA (US); Stephen A. Empedocles, Menlo Park, CA (US)

(73) Assignee: Nanosys, Inc., Palo Alto, CA (US)

(*) Notice: Subject to any disclaimer, the term of this patent is extended or adjusted under 35 U.S.C. 154(b) by 652 days.

This patent is subject to a terminal disclaimer.

(21) Appl. No.: 11/075,364

(22) Filed: Mar. 8, 2005

Related U.S. Application Data

(63) Continuation of application No. 10/826,153, filed on Apr. 16, 2004.

(60) Provisional application No. 60/463,765, filed on Apr. 17, 2003.

(51) Int. Cl.
*G01N 33/48* (2006.01)
*G01N 31/00* (2006.01)
*C12Q 1/68* (2006.01)

(52) U.S. Cl. ................................ 702/19; 702/22; 435/6

(58) Field of Classification Search .................. None
See application file for complete search history.

(56) References Cited

U.S. PATENT DOCUMENTS

| | | |
|---|---|---|
| 3,996,345 A | 12/1976 | Ullman et al. |
| 4,637,988 A | 1/1987 | Hinshaw et al. |
| 4,777,128 A | 10/1988 | Lippa |
| 5,262,357 A | 11/1993 | Alivisatos et al. |
| 5,293,050 A | 3/1994 | Chapple-Sokol et al. |
| 5,304,786 A | 4/1994 | Pavlidis et al. |
| 5,308,804 A | 5/1994 | Lee |
| 5,354,707 A | 10/1994 | Chapple-Sokol et al. |
| 5,395,791 A | 3/1995 | Cheng et al. |
| 5,422,489 A | 6/1995 | Bhargava |
| 5,492,080 A | 2/1996 | Ohkawa et al. |
| 5,499,260 A | 3/1996 | Takahashi et al. |
| 5,505,928 A | 4/1996 | Alivisatos et al. |
| 5,515,393 A | 5/1996 | Okuyama et al. |
| 5,525,377 A | 6/1996 | Gallagher et al. |
| 5,537,000 A | 7/1996 | Alivisatos et al. |
| 5,541,948 A | 7/1996 | Krupke et al. |
| 5,565,324 A | 10/1996 | Still et al. |
| 5,585,640 A | 12/1996 | Huston et al. |
| 5,625,456 A | 4/1997 | Lawandy |
| 5,674,698 A | 10/1997 | Zarling et al. |
| 5,721,099 A | 2/1998 | Still et al. |
| 5,736,330 A | 4/1998 | Fulton |
| 5,747,180 A | 5/1998 | Miller et al. |
| 5,751,018 A | 5/1998 | Alivisatos et al. |
| 5,770,299 A | 6/1998 | Dannenhauer et al. |
| 5,789,162 A | 8/1998 | Dower et al. |
| 5,845,733 A * | 12/1998 | Wolfsen .................. 340/5.53 |
| 5,985,353 A | 11/1999 | Lawton et al. |
| 5,990,479 A | 11/1999 | Weiss et al. |
| 6,114,038 A | 9/2000 | Castro et al. |
| 6,274,323 B1 | 8/2001 | Bruchez et al. |
| 6,306,610 B1 * | 10/2001 | Bawendi et al. .............. 435/7.1 |
| 6,309,701 B1 | 10/2001 | Barbera-Guillem |
| 6,319,607 B1 * | 11/2001 | Barbera-Guillem et al. .............. 428/402.24 |
| 6,355,432 B1 | 3/2002 | Fodor et al. |
| 6,602,671 B1 | 8/2003 | Bawendi et al. |
| 2002/0018632 A1 * | 2/2002 | Pelka ........................... 385/130 |
| 2004/0178338 A1 | 9/2004 | Empedocles et al. |

FOREIGN PATENT DOCUMENTS

| | | |
|---|---|---|
| WO | WO 89/10977 | * 11/1989 |
| WO | WO-9529473 | 11/1995 |
| WO | WO-9804740 | 2/1998 |
| WO | WO-9819963 | 5/1998 |
| WO | WO-9833070 | 7/1998 |
| WO | WO-9836376 | 8/1998 |
| WO | WO-9846372 | 10/1998 |
| WO | WO-9919515 | 4/1999 |
| WO | WO-0027365 | 5/2000 |
| WO | WO-0027436 | 5/2000 |
| WO | WO-0028088 | 5/2000 |
| WO | WO-0028089 | 5/2000 |

OTHER PUBLICATIONS

Cao et al. Synthesis and characterization of InAs/InP and InAs/CdSe Core/Shell Nanocrystals. Angew. Chem. Int. Ed., 1999, vol. 38, pp. 3692-3694.*

Lehmann et al. Surface plasmon dynamics in silver nanoparticles studied by femtosecond time-resolved photoemission. Physical Review Letters, 2000, vol. 85, pp. 2921-2924.*

Mahamuni et al. Spectroscopic and structural cahracterization of electrochemically grown ZnO quantum dots. Journal of Applied Physics, 1999, vol. 85, pp. 2861-2865.*

Halamka et al. A WWW Implementation of national recommendations for protecting electronic health information. Journal of the American Medical Informatics Association. vol. 4, 1997, pp. 458-464.*

Han et al. Quantum-dot-tagged microbeads for multiplexed optical coding of biomolecules. Nature Biotechnology. Jul. 2001, vol. 19, pp. 631-635.*

(Continued)

*Primary Examiner* — Marjorie Moran
*Assistant Examiner* — Russell S Negin
(74) *Attorney, Agent, or Firm* — Donna M. Fabian

(57) ABSTRACT

The compositions, methods and systems of the invention provide nanocrystal taggants for unobtrusive monitoring of objects. Objects can be tagged with nanocrystal taggant compositions for detection of informative invisible emissions on illumination with appropriate excitation wavelengths. Authentication schemes are also provided that takes advantage of the unique emission and absorption characteristics of nanocrystals to create a unique spectral code that is far more difficult to decode and replicate than those previously employed.

21 Claims, 5 Drawing Sheets

OTHER PUBLICATIONS

Kagan et al. Electronic energy transfer in CdSe quantum dot solids. Physical Review Letters, 1996, vol. 76, pp. 1517-1520.*

Takagahara T. Quantum dot lattice and enhanced excitonic optical nonlinearity. Surface Science, 1992, vol. 267, pp. 310-314.*

Chen et al. Polarization spectroscopy of single CdSe quantum rods. Physical Review B, vol. 64, 2001, pp. 245304-1 to 245304-4.*

Chung et al. Room temperature measurements of the 3D orientation of single CdSe quantum dots using polarization microscopy. PNAS, Jan. 21, 2003, vol. 100, pp. 405-408.*

Lee, S-W. et al., "Ordering of Quantum Dots Using Genetically Engineered Viruses" Science (2002) 296:892-895.

Alivisatos, A.P. "Perspectives on the Physical Chemistry of Semiconductor Nanocrystals" J. Phys. Chem. (1996) 100:13226-132396.

Alivisatos, A.P. "Semiconductor Clusters, Nanocrystals, and Quantum Dots," Science, 271:933-937 (1996).

Alivisatos, A.P. et al., "Organization of 'nanocrystal molecules' using DNA," Nature (1996) 382:609-611.

Baldwin, J.J. et al., "Synthesis of a Small Molecule Combinatorial Library Encoded with molecular Tags" J. Am. Chem. Soc. (1995) 117:5588-5589.

Bawendi, M.G. et al., "Luminescence properties of CdSe quantum crystallites: resonance between interior and surface localized states," J. Chem. Phys. (1992) 96(2):946-954.

Beverloo, H.B. et al., "Preparation and Microscopic Visualization of Multicolor Luminescent Immunophosphors," Cytometry (1992) 13:561-570.

Bruchez, M. et al., "Semiconductor Nanocrystals as Fluorescent Biological Lables" Science (1998) 281:2013-2016.

Bruchez, M. et al., "Semiconductor nanocrystals as fluorescent probes for biology," Cytometry, Supplement 9, p. 26, Mar. 1998.

Chan, W.C.W. et al., "Quantum Dot Bioconjugates for Ultrasensitive Nonisotopic Detection" Science (1998) 281:2016-2018.

Chee, M. et al., "Accessing Genetic Information with High-Density DNA Arrays" Science (1996) 274(5287):610-614.

Coffer, J.L. et al., "Characterization of quantum-confined CdS Nanocrystallites stabilized by deoxyribonucleic acid (DNA)" Nanotechnology (1992) 3:69-76.

Colvin, V.L. et al., "Light-emitting diodes made from cadmium selenide nanocrystals and a semiconducting polymer" Nature (1994) 370(6488):354-357.

Cook, "Scintillation proximity assay: a versatile high-throughput screening technology," Drug Discovery Today (1996) 1:287-294.

Correa-Duarte, M.A. et al., "Stabilization of CdS semiconductor nanoparticles photodegradation by silica coating procedure," Chem. Phys. Lett. (1998) 286:497-501.

Czarnik, A.W., "Encoding methods for combinatorial chemistry" Curr Opin Chem Biol. (1997) 1(1):60-6.

Dabbousi, B.O. et al., "Electroluminescence from CdSe quantum-dot/polymer composites" Appl. Phys. Lett. (1995) 66(11):1316-1318.

Dabbousi, B.O. et al., "(CdSe)ZnS core-shell quantum dots: synthesis and characterization of a size series of highly luminescent nanocrystallites" J. of Phys. Chem. B (1997) 101(46):9463-9475.

Danek, M. et al., "Synthesis of Luminescent Thin-Film CdSe/ZnSe Quantum Dot Composites Using CdSe Quantum Dots Passivated with an Overlayer of ZnSe" Chem. Mater. (1996) 8(1):173-180.

Egner, B.J. et al., "Tagging in combinatorial chemistry: the use of coloured and fluorescent bads" Chem. Commun. (1997) 735-736.

Empedocles, S.A. et al., "Photoluminescence Spectroscopy of Single CdSe Nanocrystallite Quantum Dots" Phys. Res. Lett. (1996) 77(18):3873-3876.

Empedocles et al., "Quantum-Confined Stark Effect in Single CdSe Nanocrystallite Quantum Dots" Science 278:2114-2117, Dec. 1997.

Fodor, S.P.A., "DNA Sequencing: Massivley Parallel Genomics" Science (1997) 277(5324):393-395.

Fox, M.A. et al., "Fluorescence and Redox Activity of Probes Anchored through an Aminotrithiol to Polycrystalline Gold" Langmuir (1998) 14:816-820.

Gan, L.M. et al., "Enhanced Photoluminescence and Characterization of Mn-Doped ZnS Nanocrystallites Synthesized in Microemulsion" Langmuir (1997) 13:6427-6431.

Gao, M. et al., "Strongly Photoluminescent CdTe Nanocrystals by Proper Surface Modification," J. Phys. Chem. (1998) 102:8360-8363.

Guha, S. et al., "Hybrid organic-inorganic semiconductor-based light-emitting diodes" J. Appl. Phys. (1997) 82(8):4126-4128.

Hines, M.A. et al., "Synthesis and Characterization of Strongly Luminescing ZnS-Capped CdSe Nanocrystals" J. Phys. Chem. (1996) 100:468-471.

Jacoby, M. "Quantum dots meet biomolecules" C&E News :8, Sep. 28, 1998.

Jarvis, R.F. et al., "Solution Synthesis and Photoluminescence Studies of Small Crystallites of Cadmium Telluride," Mat. Res. Soc. Symp. Proc. (1992) 272:229-234.

Kagan, C.R. et al., "Electronic Energy Transfer in CdSe Quantum Dot Solids," Physical Review Letters (1996) 76(9):1517-1520.

Kagan, C.R. et al., "Long-range resonance transfer of electronic excitations in close-packed CdSe quantum-dot solids," Physical Review B, 54(12):8633-8643, Sep. 15, 1996-II.

Kortan, A.R. et al., "Nucleation and Growth of CdSe on ZnS Quantum Crystallite Seeds, and Vice Versa, in Inverse Micelle Media" J. Am Chem. Soc. (1990) 112:1327-1332.

Kuno, M. et al., "The band edge luminescence of surface modified CdSe nanocrystallites: Probing the luminescing state" J. Chem. Phys. (1997) 106(23):9869-9882.

Lawless, D. et al., "Bifunctional Capping of CdS Nanoparticles and Bridging to $TiO_2$ " J. Phys. Chem. (1995) 99:10329-10335, 1995.

Lee, J-K. et al., "Surface Derivatization of Nanocrystalline CdSe Semiconductors," Mat. Res. Soc. Symp. Proc. (1997) 452:323-328.

Liz-Marzan, L.M. et al., "Synthesis of Nanosized Gold-Silica Core-Shell Particles" Langmuir, (1996) 12(18):4329-4335.

Mahtab, R. et al., "Protein-Sized Quantum Dot Luminescence Can Distinguish between 'Straight', 'Bent', and 'Kinked' Oligonucletides", J. Am. Chem. Soc. (1995) 117:9099-9100.

Mahtab, R. et al., "Preferential-absorption of a 'kinked' DNA to a newtral curved surface: comparison to and implications for nonspecific DNA-protein interactions," J. Am. Chem. Soc. (1996) 118:7028-7032.

Matsumoto, H. et al., "Preparation of Monodisperse CdS Nanocrystals by Size Selective Photocorrosion" J. Phys. Chem. (1996) 100(32):13781-13785.

McGall, G. et al., "Light-directed synthesis of high-density oligonucleotide arrays using semiconductor photoresists" Proc. Natl. Acad. Sci. USA (1996) 93:13555-13560.

Michael, K.L. et al., "Randomly Ordered Addressable High-Density Optical Sensor Arraays" Analyt. Chem. (1998) 70(7):1242-1248.

Mikulec, F.V. et al., "Synthesis and Characterization of Highly Luminescent (CdSe)ZnS Quantum Dots," Materials Research Society Symposium (1997) 452:359-364.

Mikulec, F.V. et al., Poster, Entitled "Fluorescent Semiconductor Nanocrystallites Derivatized With Biomolecules," Presented at the 216th National Meeting of the American Chemical Society Aug. 23-27, 1998.

Moran, E.J. et al., "Radio Frequency Tag Encoded Combinatorial Library Method for the Discovery of Tripeptide-Substituted Cinnamic Acid Inhibitors of the Protein Tyrosine Phosphatase PTP1B" J. Am. Chem. Soc. (1995) 117:10787-10788.

Mullenborn, M. et al., "Characterization of Solution-Synthesized CdTe and HgTe," Applied Physics (1993) 56:317-32.

Murphy, C.J. et al., "Quantum dots as inorganic DNA-binding proteins," Mat. Res. Soc. Symp. (1997) 452:597-600.

Murray, C.B. et al., "Synthesis and Characterization of Nearly Monodisperse CdE (E=S, Se, Te) Semiconductor Nanocrystallites" J. Am. Chem. Soc. (1993) 115(19):8706-8715.

Nicolaou, K.C. et al., "Radiofrequency Encoded Combinatorial Chemistry" Ingew. Chem. Int. Ed. Engl. (1995) 34(20):2289-2291.

Nirmal, M. et al., "Fluorescence Intermittency in single Cadmium Selenide Nanocrystals" Nature (1996) 383:802-804.

Pehnt, M. et al., "Nanoparticle Precursor Route to Low-Temperature Spray Deposition of CdTe Thin Films," Appl. Phys. Lett. (1995) 67(15):2176-2178.

Peng, X. et al., "Epitaxial Growth of Highly Luminescent CdSe/CdS Core/Shell Nanocrystals with Photostability and Electronic Accessibility," J. Am. Chem. Soc. (1997) 119:7019-7029.

Peng, X. et al., "Synthesis and Isolation of a Homodimer of Cadmium Selenide Nanocrystals," Angewandte Chemie (1997) 36:145-147.

Plunkett, M.J. et al., "Combinatorial chemistry and new drugs" Sci Am (1997) 276(4):68-73.

Rajh, T. et al., "Synthesis and Characterization of Surface-Modified Colloidal CdTe Quantum Dots" J. Phys. Chem. (1993) 97:11999-12003.

Rogach, A.L. et al., "Synthesis and characterization of Thiol-Stabilized CdTe Nanocrystals" Ber. Bunsenges. Phys. Chem. (1996) 100(11):1772-2778.

Sambrook, J. et al., Molecular Cloning: A Laboratory Manual: Second Edition, Cold Spring Harbor Press, p. 12.14, 1989.

Schrock, E. et al., "Multicolor Spectral Karyotyping of Human Chromosomes," Science (1996) 273:494-497.

Service, R.F. "Semiconductor Beacons Light Up Cell Structures" Science (1998) 281:1930-1931.

Spanhel, L. et al., "Photochemistry of Colloidal Semiconductors. Surface Modification and Stability of Strong Luminescing CdS Particles" J. Am. Chem. Soc. (1987) 109(19):5649-5655.

Steigerwald, M.L. et al., "Surface Derivatization and Isolation of Semiconductor Cluster Molecules," J. Am. Chem. Soc. (1988) 110:3046-3050.

Wang, D.G. et al., "Large-Scale Identification, Mapping, and Genotyping of Single-Nucleotide Polymorphisms in the Human Genome" Science (1998) 280:1077-1082.

Whitesell, J.K. et al., "Directionally Aligned Helical Peptides on Surfaces" Science (1993) 261:73-76.

Winzeler, E.A. et al., "Direct Allelic Variation Scanning of the Yeast Genome" Science (1998) 281:1194-1197.

Zhang, Y-Z. et al., "Novel Flow Cytometry Compensation Standards: Internally Stained Fluorescent Microspheres With Matched Emission Spectra and Long-Term Stability," Cytometry (1998) 33:244-248.

* cited by examiner

NANOCRYSTAL TAGGANTS

CROSS-REFERENCE TO RELATED APPLICATION

This application is a continuation-in-part of U.S. patent application Ser. No. 10/826,153, filed Apr. 16, 2004, which claims priority to and benefit of U.S. Provisional Patent Application No. 60/463,765, filed Apr. 17, 2003 each of which is incorporated herein by reference in its entirety for all purposes.

COPYRIGHT NOTIFICATION

Pursuant to 37 C.F.R. §1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates generally to non-obtrusive taggants. The invention provides methods, compositions and systems for tagging objects with fluorescent nanocrystals having emission wavelengths outside the visible light spectrum.

Labels, markers and computer readable encoding have historically been used to provide detection and identification of materials and products. For example, farm animals are branded, adhesive backed labels are applied to containers of goods, fluorescent markers are linked to biomolecules, and bar-codes are imprinted on retail product packaging. These unambiguous marks can provide identification and/or tracking of otherwise indistinguishable objects.

The Universal Product Code (the familiar "bar code" seen on many retail products) provides a way to label the surface of a product with scanable identification numbers for quick input into a computer system and confident identification of the product. The barcodes can represent numbers so large that most errors in reading can be detected as numbers not assigned to any product. Bar code scanning can be automated, or semiautomated, to increase the efficiency of product handling operations while increasing the accuracy of documentation. The introduction of laser scanable bar code technology has provided great benefits in product sales and inventory control. However, bar Semiconductor nanocrystals have been developed that have a great number of interesting properties, including optoelectronic and luminescent properties. In particular, the quantum confinement effects exhibited by semiconductor nanocrystals can be exploited both electronically and optically. For example, when an appropriate nanocrystal is impinged upon by a photon, an electron in the nanocrystal can be displaced from its orbital, giving rise to a free electron and a hole (an "exciton") within the nanocrystal. By shuttling the separated charges to different locations, e.g., different electrodes, one can exploit the potential energy of the separated charges, e.g., in generation of an electrical current. The separation of charges has provided the basis for use of nanocrystals in nanocomposite based photovoltaic applications. In particular, Alivisatos et al., have described the use of semiconductor nanocrystals in a hole conducting matrix to provide a photoactive layer for a photovoltaic device, in place of a bulk silicon substrate or amorphous silicon substrate. Such devices purportedly offer theoretical advances in manufacturability, efficiency, and flexibility over conventional photovoltaics.

When an exciton is allowed to recombine with the electron structure of the nanocrystal, light can be emitted (fluoresced) from the nanocrystal at a longer wavelength than the initial excitation wavelength. The wavelength of the emitted light can is related to the size of the nanocrystal. By adjusting the size and composition of the nanocrystal, one can produce crystals that have any of a variety of different absorption (excitation) and/or emission spectra. These fluorescent properties have been described for use as detectable markers, e.g., for use in biological and/or chemical assays, such as in nucleic acid experimentation (see, U.S. Pat. No. 6,274,323, "Method of Detecting an Analyte in a Sample Using Semiconductor Nanocrystals as a Detectable Label", to Bruchez, et al.). Nanocrystal mixtures with resolvable absorption and/or emission spectra have been suggested for use as taggants, e.g., as additives to a particular material or product to facilitate understanding of the origins and ultimate destination of such materials or products (see, e.g., Published U.S. Patent Application No. 20020160412, "Inventory Control", by Bawendi et al., which is incorporated herein by reference in its entirety for all purposes). In particular, using mixtures of nanocrystals has been suggested as a substitute for barcoding in applications where written codes are not desirable or practicable, e.g., for small or irregular items, ornamental items, for fluid materials, or for component elements of greater mixtures. However, proposed nanocrystal taggant systems can be difficult to detect in many materials or through obstructions. What's more, where secrecy is important, current technologies undesirably warn observers with colored scanning lights or obvious emissions from the labeled object.

In view of the above, a need exists for a non-obtrusive labeling system that does not visibly mark the tagged object, or obviously broadcast the scanning activities. It would be desirable to have scanning technologies that can detect tags through certain barriers or obscured lines of sight. The present invention provides these and other features that will be apparent upon review of the following.

SUMMARY OF THE INVENTION

The present invention provides methods, compositions and systems for nonobtrusive monitoring of objects. The compositions can include, e.g., fluorescent nanocrystals with light excitation and emissions at nonvisible wavelengths and disposed in an adherent matrix or in solution for injection. Methods of the invention provide monitoring of an object by, e.g., tagging the object with a taggant composition of nanocrystals, exciting the nanocrystals and detecting nonvisible light emitted from the nanocrystals. Systems of the invention for nonobtrusive monitoring can include, e.g., nanocrystal compositions of the invention tagged to an object, a light source providing excitation wavelengths, a light detector receiving light emitted from the tag and communicating with a logic device which can interpret detector signals to monitor the presence, location or identity of the object.

Methods of monitoring an object, in the invention can include, e.g., providing a composition with a population of nanocrystals that emit nonvisible light when excited, tagging the object with the composition, exciting the nanocrystals on the tagged object to emit the light, and detecting the nonvisible light emitted from the composition to monitor the object. The object can be, e.g., an article, a material, an article of commerce, an analytical sample, an animal, a medical device, and/or the like. The nanocrystals can be, e.g., a semiconductor, a nanodot, a nanorod, a branched nanorod, a nanowire, a nanocrystal, a coated nanocrystal, a passivated nanocrystal, and/or a derivitized nanocrystal. Exciting can be by, e.g., illuminating the object with an ultraviolet light source, visible light source, or infrared light source. Emission wavelengths can be, e.g., nonvisible light, such as UV or IR wavelengths.

Nanocrystals used in the methods of the invention are generally fluorescent semiconductors. The nanocrystals can be manufactured, e.g., by colloidal synthesis, precipitation, monolayer self assembly, photolithography, VLS growth, gas-phase nucleation and growth, solution-phase nucleation and growth, or vapor deposition. Nanocrystals used as taggants can be, e.g., a mixed population of a nanocrystal subsets with unique excitation and emission characteristics. A population of nanocrystals can include, e.g., two or more subsets of nanocrystals with different light emission properties. Methods can include, e.g., tuning the nanocrystals to adjust excitation wavelengths, excitation polarity angles, emission wavelengths, emission polarity angles, emission spectral width, or intensity of emissions. Methods of tuning nanocrystal characteristics can include controlling, e.g., the size of the nanocrystals, the shape or pattern of the nanocrystals, the polarization of the nanocrystals, the size-distribution of the nanocrystals, the composition of the nanocrystals, the mass percentage of a nanocrystal constituent, and/or the representation of a nanocrystal subset. A population of nanocrystals can contain, e.g., two or more subsets of nanocrystals having one or more different excitation wavelengths. Nanocrystals of the method can be modified for special environments and tagging tasks by linking them, e.g., to a biomolecule, an insulating molecule, a hydrophilic molecule, a hydrophobic molecule, solid support, and/or the like.

Nanocrystal taggants of the methods can be associated with an adherent matrix, e.g., useful in tagging the nanocrystals to an object. For example, the nanocrystals can be coated onto a substrate material to produce a label, tag, decal, etc. The adherent matrix can be any substance useful in attaching or incorporating taggant to an object, such as, e.g., a polymer, a glass, a crystal, an organic material, an inorganic material, a liquid, a penetrant, a solid support, tape, a patch, a fiber, a capsule, a powder, a decal, a pin, a clip, a label, ink, an adhesive, and/or the like.

Nanocrystal taggants of the methods can be tagged to objects in a fashion appropriate to the particular object and monitoring environment. For example, tagging can comprise depositing, spraying, brushing, taping, combining, mounting, injecting, blending, wiping, vaporization and deposition, painting, inscribing, stamping, sticking, pinning, or applying the composition into or onto the object. Additional visible or invisible information can be provided in a tag by, e.g., applying the composition to the object in a meaningful or unique shape or pattern. An object history or updated status can be provided by, e.g., cumulatively tagging the object over time with additional nanocrystal subsets.

A variety of light sources and detectors can be used to monitor an object. For example, the light source can be a laser, a light emitting diode, an incandescent lamp, a mercury vapor lamp, a deuterium lamp, a defraction grating, a prism, a light filter, the sun, fluorescence from other molecules in the composition, and/or the like. Sensors for detecting emissions can be, e.g., a light sensor, a photodiode, a CCD, a CMOS sensor, a photodiode array, a photomultiplier tube, a fluorometer, a detector array, an image array, a camera, a spectrophotometer, the eye of an observer, and/or the like.

Information encoded in compositions of the invention can be decoded by evaluating spectral patterns of emissions to identify or locate an object. Decoding can comprise evaluating (deconvoluting) excitation wavelengths, excitation polarization angles, emission frequencies, emission frequency combinations, emission shapes or patterns, emission polarization angles, emission intensities, and/or emission spectral widths. Decoding is commonly accomplished using a logic device, such as a computer.

Methods of the invention can be used to monitor objects through a barrier. Barriers can be, e.g., living tissue, organic tissue, vegetation, animals, smoke, screens, dust, plastics, clouds, rain, water, a fabric, a material that transmits nonvisible light, and/or visibly obscured lines of sight. In one aspect, monitoring through a barrier can be accomplished by, e.g., illumination with IR light to excite nanocrystals and detection by receiving IR light.

Compositions of the invention can be, e.g., a nanocrystal population with a single subset of naked semiconductor nanodots, or a complex population of many nanocrystal subsets having data encoded in a matrix of multiplexed emissions characteristics. The compositions can be disposed in or on a variety of supports or matrices suitable for particular tagging tasks.

For example, compositions can be a population of nanocrystals disposed in an adherent matrix or suspended in a solution suitable for administration to a mammal, and having an excitation spectrum and an emission spectrum at least a portion of which is in the nonvisible range. Such nanocrystals can be, e.g., a semiconductor, a nanodot, a nanorod, a nanocrystal, a nanowire, a branched nanorod, a coated nanocrystal, a passivated nanocrystal, a derivitized nanocrystal, and/or the like. The nanocrystals can have a diameter ranging from about 1000 nm to about 0.1 nm, or ranging from about 50 nm to about 15 nm. The nanocrystals inner core can be coated with a layer of semiconductor having a band gap greater than that of the core, e.g., to enhance the emissions efficiency and/or to narrow the emissions bandwidth, generally referred to as a Type-I band gap offset. Alternatively, such core-shell nanocrystals may comprise a type-II band gap offset, where electrons and holes localize differentially to the core or shell material, and emissions derive from recombination at the interface of the materials. Such Type-II band gap materials are described in Kim et al., J. Am. Chem. Soc. 2003, 125: 11466-11467, which is incorporated herein in its entirety by reference.

Nanocrystals of the composition can be made up of, e.g., core crystals, coatings, and/or, linker groups. For example, the nanocrystals can be composed of ZnS, ZnSe, ZnTe, CdS, CdSe, CdTe, GaN, GaP, PbTe, HgS, HgSe, HgTe, CdTe, GaAs, GaSb, InP, InAs, InSb, AlS, AlSb, PbS, PbSe, Ge, Si, and/or the like. Nanocrystal cores can be coated with layers of material, such as AlAs, AlN, AlP, AlSb CdO, CdS, CdSe, CdTe, GaAs, GaN, GaP, GaAs, GaSb, HgO, HgS, HgSe, HgTe, InAs, InN, InP, InSb, MgS, MgSe, ZnO, ZnS, ZnSe, ZnTe, and/or the like. Nanocrystals can have linker binding groups or other appropriate chemical reactive groups to participate in linkage chemistries (derivitization) with linking agents such as, substituted silanes, diacetylenes, acrylates, acrylamides, vinyl, styryls, silicon oxide, boron oxide, phosphorus oxide, N-(3-aminopropyl)3-mercapto-benzamide, 3-aminopropyl-trimethoxysilane, 3-mercaptopropyl-trimethoxysilane, 3-maleimidopropyl-trimethoxysilane, 3-hydrazidopropyl-trimethoxysilane, hydroxysuccinimides, maleimides, haloacetyls, pyridyl disulfides, hydrazines, ethyldiethylamino propylcarbodiimide, and/or the like.

Nanocrystal compositions can be prepared to provide a variety of distinguishable properties. Nanocrystals of the compositions can be manufactured, e.g., by colloidal synthesis, precipitation, monolayer self assembly, photolithography, VLS growth, gas-phase nucleation and growth, solution-phase nucleation and growth, vapor deposition, and/or the like. The compositions can have populations of nanocrystals with predetermined excitation spectra or emission spectra. Predetermined spectra can be provided by varying, e.g., a size of a nanocrystal, a constituent semiconductor, a size-distribution of nanocrystals, a composition of a nanocrystal, a polarization of a nanocrystal, or a concentration of a nanocrystal constituent. Mixed populations of nanocrystals can be encoded by provision of two or more subsets of nanocrystals having different light emission wavelengths. Subsets of a population of nanocrystals can emit light within a spectral width from less than about 25 nm to more than about 30 nm, or the subsets can be distinguishable by having a broad emissions bandwidth character. Nanocrystal subsets can be have a characteristic excitation spectrum (or wavelengths), e.g., in the ultraviolet, visible, or infrared regions. A population of nanocrystals can include two or more subsets of nanocrystals with different excitation wavelengths such that, e.g., the emissions of the population can have different wavelengths or different wavelength intensities when alternately excited with the different excitation wavelengths. The emissions can be, e.g., in ultraviolet or infrared wavelengths. The populations can include a subset of nanocrystals having, e.g., predetermined and decodable intensities of emission at certain wavelengths; such intensities can be controlled by varying, e.g., a concentration of a nanocrystal constituent, the presence of an overcoating, and/or the numeric representation of nanocrystals in the subset.

Nanocrystal compositions can be formulated with appropriate solutions for administration to animals. Administration a mammal can include delivery of the nanocrystals through intravenous, intramuscular, intraperitoneal, intracerebrospinal, subcutaneous, intraarticular, intrasynovial, intrathecal, oral, topical, intranasal, and/or pulmonary routes. Nanocrystals can be administered to animals, e.g., to track gastrointestinal movements, to provide images of body cavities, as marker groups linked to affinity molecules targeting tissue pathologies, as coded identification capsules, and the like.

Nanocrystals of the methods and compositions can be disposed in an adherent matrix, e.g., to facilitate tagging of objects. Adherent matrices can be, e.g., polymers, penetrants, solid supports, glass, crystals, organic materials, inorganic materials, liquids, tape, fibers, patches, capsules, powders, decals, pins, clips, labels, ink, adhesives, and/or the like.

Compositions of the invention can be excitable or detectable with light wavelengths adapted for transmission through barriers. Barriers can be, for instance, living tissue, organic tissue, vegetation, animals, smoke, screens, dust, plastics, clouds, rain, water, a fabric, a material that transmits nonvisible light, visibly obscured lines of sight, and/or the like.

Systems of the invention can include, e.g., compositions, hardware, and software to for nonobtrusive monitoring of objects. Monitoring systems can include, e.g., a composition of a population of nanocrystals tagged to an object and having excitation wavelengths and nonvisible light emission wavelengths, a light source adapted to excite the nanocrystals at the excitation wavelengths, a light detector adapted to detect light emitted from the nanocrystals, and a logic device in communication with the detector and adapted to interpret detector signals for monitoring of a presence, identity and/or location of the composition and object. Systems for monitoring can be configured, for example, to monitor the location of retail articles, to monitor analytical samples, to monitor the identity or location of objects in transit, or to monitor the identity or location of objects within living tissue.

Nanocrystals of the system can be, e.g., semiconductor materials having nanodimensions (from about 1000 nm to less than about 0.1 nm). The nanocrystals can be, e.g., semiconductors, nanodots, nanorods, nanowires, nanocrystals, branched nanorods, coated nanocrystals, passivated nanocrystals, and/or derivitized nanocrystals. A population of nanocrystals can include, e.g., two of more subsets of nanocrystals having different light emission wavelengths and/or different light emission intensities.

Systems of the invention can include a light source to illuminate and excite taggant compositions on objects being monitored. Light sources can have adequate intensity and appropriate wavelength to excite taggant compositions. For example, light sources can include lasers, light emitting diodes, incandescent lamps, mercury vapor lamps, deuterium lamps, defraction gratings, prisms, light filters, the sun, fluorescence from other molecules in the composition, and/or the like.

Light detectors of the systems can receive emissions from illuminated taggant compositions. Light detectors can include, e.g., light sensors, photodiodes, charge coupled devices (CCDs), complimentary metal oxide silicon (CMOS) sensors, photodiodes arrays, photomultiplier tubes, fluorometers, detector arrays, image arrays, cameras, spectrophotometers, the eyes of an observer, and/or the like.

Logic devices of the system can include computers and interfaces to receive and interpret signals from the light detectors. Logic devices can interpret signals, e.g., by decoding emissions spectral patterns or multiplexed information, by displaying appropriate massages to a system operator, and/or by storing data memorializing detection events for later retrieval or evaluation. Logic devices of the systems can include, e.g., software with decoding algorithms, analog displays, digital displays, computer systems, and/or the like.

In one embodiment, a method of encoding and authenticating a nanocrystal spectral code is disclosed which generally comprising the steps of providing a composition comprising a population of nanocrystals that emit light when excited; determining at least one emission wavelength profile of the composition when excited with a select numeric excitation wavelength to encode a unique spectral code for the nanocrystal composition; tagging at least a first object with the composition; exciting the nanocrystal composition on the first and/or a second tagged object with the at least one select excitation wavelength; and detecting the emission wavelength profile emitted from the first and/or second tagged object, thereby determining whether the tagged object has the unique spectral code.

An aspect of the system can be, e.g., a barrier between the object or composition and the light source or the light detector. Exemplary barriers can include, e.g., living tissue, organic tissue, vegetation, animals, dust, plastics, smoke, clouds, rain, water, a screen, a fabric, a material that transmits nonvisible light, or visibly obscured lines of sight. Excitation and emission wavelengths can be selected for penetration of particular barriers.

Definitions

Before describing the present invention in detail, it is to be understood that this invention is not limited to particular compositions, methods, or systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "an object" can include a combination of two or more objects; reference to "a matrix" can include mixtures of matrices, and the like.

Unless defined otherwise, all technical and scientific terms used herein have the same meaning as commonly understood by one of ordinary skill in the art to which the invention pertains. Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

The term nanocrystal, as used herein, refers to semiconductor crystals having a length, width, or height dimension in the nanometer range (i.e., less than about 1000 nm). Nanocrystals of the invention can include, e.g., nanoscale dots, tetrapods, rods, teardrops, bars, nanofibers, nanowires, sheets, and/or the like.

The term object, as used herein, refers any solid, liquid, gel, powder, or molecular material capable of permanently or temporarily being tagged with nanocrystal taggants. Solid material objects can include, e.g., retail items, manufactured goods, animals, grains, powders, vehicles, and the like. Liquid materials can include, e.g., chemicals, process intermediates, solutions, microfluidic samples or buffers, and the like. Molecular material objects can include, e.g., members of molecular libraries, biomolecules, and the like.

A population of nanocrystals, as used herein, refers to two or more nanocrystals. A subset refers to one or more nanocrystals of a nanocrystal population having detectable characteristics in common, such as, e.g., excitation wavelengths, excitation polarization, emission polarization, emission wavelength, emission intensity, and/or emission spectral width.

An adherent matrix, as used herein, refers to any material associated with taggant nanocrystals which can facilitate tagging of an object. For example, adherent matrices can include solids, liquids, powders, gels, adhesives, solid supports, affinity molecules, solid substrates, glass, crystals, plastics, tapes, fibers, decals, labels, pins, clips, penetrants, inks, surfactants, polymers, pellets, and/or the like.

DETAILED DESCRIPTION

Figure 1A:
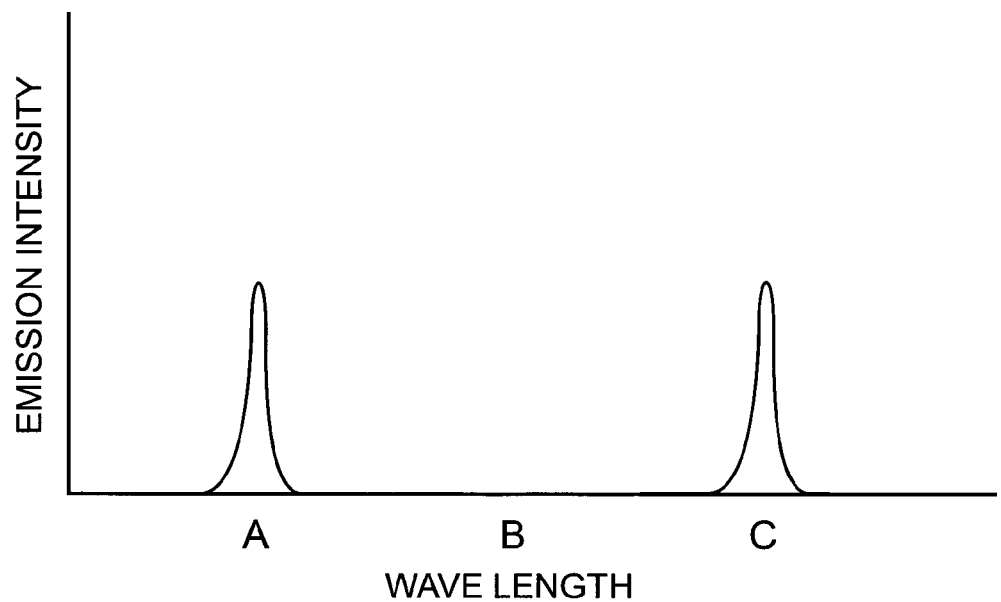
FIG. 1 is a schematic diagram of unique emission wavelength combinations that can be encoded by nanocrystal subsets in a taggant composition.

In general, the present invention provides novel methods of using semiconductor nanocrystals in the monitoring of objects or materials, compositions for unobtrusive monitoring of objects, and systems for monitoring objects tagged with nanocrystals emitting nonvisible light. In particular, the present invention employs populations of nanocrystals that present novel combinations of absorption and emission spectra to provide advantages over previously described monitoring, tagging, and inventory control methods. Of particular advantage are uses of semiconductor crystals that absorb and emit in nonvisible light regimes that allow for a number of advantages, including nonobtrusive monitoring, monitoring through organic material, e.g., in vivo monitoring, monitoring through foliage, and/or the like. Systems are described to practice methods of the invention.

The present invention provides compositions, methods and systems, e.g., to unambiguously and unobtrusively label (or tag) objects with fluorescent nanocrystals. Nanocrystal compositions having nonvisible fluorescent emissions can be associated with objects (such as, e.g., products, articles, or materials) to provide, e.g., distinct combinations of light emission wavelengths, polarizations, and/or intensities decodable to identify the object. Objects tagged with nanocrystal compositions can be excited, e.g., by illumination with appropriate nonvisible excitation light wavelengths and the resultant emissions detected by appropriate light sensitive instrumentation. Systems adapted to implement nanocrystal based methods of the invention can provide, e.g., light sources to excite nanocrystal compositions tagged to an object, light detectors to detect emissions from the nanocrystals, and logic devices capable of interpreting signals transmitted from detectors.

Objects can be tagged with nanocrystals to identify and/or locate the objects in diverse processes ranging, e.g., from inventory control, to security monitoring, to visualizing living tissue, to labeling members of molecular synthesis libraries. The advantage of nonvisible excitation and emissions can include the ability to detect the nanocrystals through obscuring barriers, reduced distraction or interfering background during scanning, increased resolution of scanning, and concealment of scanning activities to unauthorized observers.

Compositions of the Invention

Compositions of the invention can include, e.g., nanocrystals disposed in an adherent matrix. The population of nanocrystals can have, e.g., a predetermined excitation and/or emission spectrum in the nonvisible range uniquely identifying that population. The adherent matrix can be, e.g., a solid or fluid substance adapted for tagging the nanocrystals to a particular object.

Nanocrystals

Nanocrystals of the invention are generally, e.g., semiconductor crystals, having a dimension in the nanometer range, that are capable of emitting a specific invisible light wavelength in response to excitation by an appropriate excitation light wavelength. Combinations of two or more nanocrystal subsets with different light emission properties (e.g., emission frequencies and/or intensities) can provide encoding possibilities for large numbers of unique emission spectra. Nanocrystals can be fabricated to include a variety of, e.g., crystal sizes, size ranges, polarizations, crystal compositions, linkage chemistries, coatings, and/or the like. The diversity of nanocrystals described here can provide tags well adapted to a large variety of uses in monitoring objects.

The main active component in the compositions of the present invention, are populations of nanocrystals that have absorption spectra (excitation wavelengths) and emission spectra that fit the requirements of the invention, e.g., have a component of the absorption spectrum that is in the desired range and an emission spectrum that is in the nonvisible range. For example, the nanocrystals can absorb in the UV, visible, IR (near-IR, mid-IR and/or far-IR), and emit in the UV or IR spectrum. A nanocrystal that emits in one range of wavelengths can absorb light in that same range (but at a longer wavelength), or optionally, can absorb in a range of higher energy than emissions (e.g., absorb in the visible and emit in the IR). In many embodiments of the invention, near-IR emission is preferred, as is near-IR absorption. Preferred nanocrystal compositions can have an absorption spectrum that is in the UV, visible or near IR range, with an emission spectrum that is within the near IR to IR range. In particularly preferred aspects, nanocrystals that absorb in the UV or near IR range and emit in the near IR range are preferred, with near IR absorbing and emitting nanocrystals being most preferred for many embodiments.

The excitation wavelengths, polarization properties, emission wavelengths, and emission spectral width of individual nanocrystals or subsets can be controlled (tuned) by adjustment of certain manufacturing specifications to encode nanocrystals with predetermined characteristics. For example, the choice of nanocrystal size, nanocrystal shape, size-distribution, composition, the mass percent of a nanocrystal constituent, the choice of constituent semiconductor, linkage chemistries, and/or coatings can tune characteristics used to encode nanocrystal subsets.

The size of nanocrystals can affect the excitation and emission wavelengths of the nanocrystals. Useful semiconductor nanocrystals generally have one or more dimension, e.g., comparable to, or smaller than, the exciton Bohr radius of the bulk crystal. Quantum confinement of both electron and hole (exciton) in a space smaller than the bulk exciton Bohr radius (e.g., in crystals in the nanometer range) can lead to an increase in the effective band gap of the material with decreasing crystallite size. Consequently, both optical absorption and emission of these nanocrystals can shift to the higher energy levels (blue shift). In addition, such quantum confinement in a nanocrystal can provide a narrow (more precise) Gaussian emission profile, e.g., less than 25 to 30 nm. In a population or subset of nanocrystals, the overall emission spectrum can be indicative of, e.g., the distribution of constituent nanocrystal sizes.

The nanocrystals of the invention can be, e.g., sheets, wires, or dots with a dimension (thickness or diameter) in the nanometer range. For example, nanocrystals can range in diameter from about 1000 nm to about 0.1 nm, from about 100 nm to about 1 nm, from about 50 nm to about 1.5 nm, or about 15 nm. Preferred nanocrystal diameters can be, e.g., about 50 nm, 35 nm, 25 nm, or about 10 nm. The precision of diameter sizing in a subset of nanocrystals can affect the range of emissions (spectral width) of that subset. In some embodiments of the invention, information can be encoded as emission spectral widths (i.e., with relatively narrow bandwidth nanocrystal subsets being distinguishable from relatively broad bandwidth nanocrystal subsets).

The materials making up nanocrystals can affect excitation and emission wavelengths. Semiconductor nanocrystals can be fabricated from a variety of different constituent semiconductor materials, including, e.g., Group III-V, Group II-VI and Group IV semiconductors, e.g., ZnS, ZnSe, ZnTe, CdS, CdSe, CdTe, GaN, GaP, GaAs, GaSb, InP, InAs, InSb, AlS, AlSb, PbS, PbSe, PbTe, HgS, HgSe, HgTe, Ge and Si, depending upon the desired application. Nanocrystals that typically emit in the near IR range include, e.g., InP, InAs, InSb, HgS, HgSe, HgTe, PbS, PbTe, CdTe, Si, Ge, and PbSe. Nanocrystals that typically emit light in the UV or near UV range include, e.g., ZnS, ZnSe, CdS, and GaN.

Nanocrystals can be coated to affect emission wavelengths and/or to increase the efficiency of emissions. As described in U.S. Pat. No. 6,251,303, "Water-Soluble Fluorescent Nanocrystals", to Bawendi, et al., nanocrystals can be coated, e.g., with a layer of hydrophobic linker having hydrophilic tips to provide insulation against electron transfer to aqueous environments while the nanocrystals remain suspendable or soluble in water. Nanocrystal emissions efficiency can optionally be improved by overcoating with a semiconductor material having a band gap greater than that of the underlying nanocrystals. An overcoating layer at the surface of the nanocrystal can fill defects that can result in traps for electrons or holes. An insulating layer at the surface of the nanocrystal can provide an atomically abrupt jump in the electrical potential at the interface which eliminates energy states that can serve as traps for the electrons and holes. This results in higher fluorescent efficiency, i.e., higher conversion of excitons to release of fluorescent emissions. In one embodiment, for example, a CdSe nanocrystal is overcoated with ZnS to enhance the fluorescent emissions from the excited CdSe "core". See, Published U.S. Patent Application No. 2002-0160412, "Inventory Control", to Bawendi. Alternatively, as noted previously, materials that include a type-II band gap offset may be employed as emissive compositions of the invention. See Kim et al., J. Am. Chem. Soc. 2003, 125: 11466-11467, previously incorporated herein by reference. Exemplary semiconductor overcoats to enhance the efficiency of nanocrystals of the invention can include AlAs, AlN, AlP, AlSb, CdO, CdS, CdSe, CdTe, GaAs, GaN, GaP, GaAs, GaSb, HgO, HgS, HgSe, HgTe, InAs, InN, InP, InSb, MgS, MgSe, ZnO, ZnS, ZnSe, ZnTe, and/or the like.

Nanocrystals can be fabricated in a variety of ways to produce nanocrystals of various shapes, compositions and sizes. For example, nanocrystals can be nanosheets, nanowires, branched nanowires, or nanodots. In addition, the nanocrystals can comprise a single homogeneous structure, or they can comprise heterogeneous structures, e.g., as a core-shell, longitudinal heterostructure, or core-branch heterostructure. Such nanocrystals can be produced, e.g., by photolithography and deposition (e.g., Published U.S. Patent Application 2002-0104762, "Methods for the Manufacture of Colloidal Rod Particles as Nanobar Codes", to Stonas, et al.), precipitating reactions in a coordinating solvent (e.g., Published U.S. Patent Application 2002-006640, "Synthesis of Colloidal Nanocrystals", to Peng, et al.), by providing self assembling monolayers (e.g., U.S. Pat. No. 5,751,018, "Semiconductor Nanocrystals Covalently Bound to Solid Inorganic Surfaces Using Self-Assembled Monolayers", to Alivisatos, et al.), vapor deposition to seeded semiconductors, vapor-liquid-solid (VLS) growth, gas-phase nucleation and growth, solution-phase nucleation and growth, and/or the like. By way of example, CdSe nanocrystals can be prepared by mixing a cadmium containing compound, e.g., $CdO_2$, $Cd(acac)2$ or other cadmium containing salt, with a reducing agent in the presence of surfactant, e.g., tri-octyl phosphine (TOP), to provide a cadmium containing precursor material. The Cd precursor can then be mixed with a Se donor, e.g., TOP:Se. This mixture can then be added to a surfactant mixture that includes an amine, e.g., 1-hexadecylamine, at elevated temperatures to initiate crystal nucleation and growth.

Optionally, nanocrystal surfaces can be populated with desirable chemical and/or binding groups, e.g., by linker reaction chemistries. Specific affinity molecules can be bound to the surface of nanocrystals through the use of linker chemistries. For example, dopants, substrate molecules, or applied coatings can provide linker reactive groups, such as amines, sulfhydryls, carboxylic acids, alcohols, aldehydes, and thiols, that can covalently bond to commercially available bivalent linker molecules. Binding groups can be cross-linked to nanocrystals using linkage chemistries including, e.g., bivalent linker chains having terminal hydroxysuccinimide (reactive with primary amines), maleimides, haloacetyls, pyridyl disulfides (reactive with sulfhydral groups), hydrazines (reactive with aldehydes), ethyldiethylamino propylcarbodiimide (EDC, reactive with carboxyl groups). Nanocrystals can be passivated, e.g., by coating the semiconductor surface with a surfactant, e.g., tri-octyl phosphine (TOP) to reduce the interference of ionic reactions with the crystal. Hydrophobic insulating layers and hydrophilic solubilizing layers can be incorporated onto nanocrystals as described in Bawendi '303, cited above. Linkage chemistries can be employed, e.g., to link the nanocrystals to biomolecules, affinity molecules, insulating molecules, hydrophilic molecules, hydrophobic molecules, solid supports, and/or the like.

Significant information can be imparted by a nanocrystal taggant preparation having a uniform set of nanocrystals. Intensity, wavelength, polarization, bandwidth characteristics of a nanocrystal subset, alone or in combination, can encode substantial amounts of information. A taggant composition of similar nanocrystals can emit light in a narrow band width, such as in a Gaussian distribution with a width at half maximum signal of less than about less than about 100 nm, 75 nm, 50 nm, 40 nm, or about 25 nm, to allow a large number of possible wavelengths within a spectrum. The "bases" of such distributions can overlap significantly while distribution "peaks" remain electronically resolvable. For example, it is possible to distinguish the center wavelength or peak-wavelength of a nanocrystal subset with an accuracy of less than 1 nm. Nanocrystal subsets with a bandwidth of 25 nm can therefore provide more than about 600 resolvable emission signals in the near IR (from about 700 nm to about 1300 nm). Far more unique emission signals could be uniquely encoded by uniform preparations of nanocrystals in larger bands of the spectrum, such as parts of the far infrared (e.g., 6000 nm to about 40,000 nm). The width of the emission distribution can be influenced by, e.g., the size heterogeneity of the population of nanocrystals in the preparation. Encoding possibilities for a single nanocrystal subset can rise exponentially when the subset can be tuned to have unique combinations of emission characteristics (wavelength, intensity, bandwidth, polarization, etc.).

The number of unique emission spectra for nanocrystal compositions can be further expanded exponentially, e.g., by preparing population mixtures including two or more subsets of nanocrystals. For example, a composition of nanocrystals prepared from a mixture of two uniform nanocrystal subsets, each displaying emission wavelengths within a narrow band of the near IR spectrum can provide more than about 179,700 (600C2) unique emission wavelength signal combinations. By increasing mixture to 3 allowable nanocrystal subsets, the number of possible combinations increases to 35,820,200 (600C3). Those skilled in the art will appreciate that the number of possible combinations rapidly increases to astronomical values as the number of allowable coding subsets increases. Compositions having a population of mixed nanocrystal subsets can provide spectra encoding a huge number of unique emission signal combinations. These numbers can be further expanded by encoding each subset with multiple emissions characteristics, as discussed above.

The Intensity of nanocrystal emissions can provide decodable information from compositions of the invention. The intensity of nanocrystal emissions can be varied or predetermined, e.g., by tuning the crystal constituents, emissions efficiency, excitation polarization, or the amount (representation) of a nanocrystal subset in the population of nanocrystals in the taggant composition. In one embodiment, a reference nanocrystal subset can be present in the taggant composition as a standard of comparison to increase precision in determination of the relative emissions intensities at encoded wavelengths. At a given emission wavelength, e.g., 10 or more relative (or absolute) intensities can be detected and resolved. In such a case, the amount of information encodable within any given emission wavelength can be increased, e.g., 10-fold. Encodable information for a population of four nanocrystal subsets can be increased, e.g., at least $10^4$-fold, etc.

Emissions bandwidth can be shared between two or more nanocrystal subsets by, e.g., providing populations that respond to different excitation wavelengths. This can also increase the amount of information encodable in the nanocrystal population. For example, a first population subset of nanocrystals can display UV excitation wavelengths and a second population subset of nanocrystals can display IR excitation wavelengths. Although the emission spectra of the two populations can overlap, they can be detected and unambiguously decoded separately by illuminating the populations first with one excitation wavelength, then with the other excitation wavelength.

In another embodiment, emissions bandwidth can be shared between subsets of nanocrystals, e.g., sharing a common excitation wavelength but having different emission polarization angles. For example, one population of nanocrystals in a mixed composition can absorb or emit linearly polarized light at certain emissions wavelengths and another subset in the mixed composition can emit plane polarized light at the same emission wavelengths. By selecting and comparing emitted wavelength or intensities at predetermined angles, e.g., using polarized light filters, the emissions of some subsets can be detected (and interpreted) separately from emissions of other subsets, e.g., while using the same excitation wavelengths. Nanocrystals can be tuned to practice such an embodiment by, e.g., preparing populations of rod like nanocrystals (emitting linearly polarized emissions) and populations of nanospheres (emitting plane polarized emissions), see Hu, J. T.; Wang, L. W.; Li, L. S.; Yang, W. D.; Alivisatos, A. P., J. Phys. Chem. B 2002, 106, 2447-2452. In another embodiment, further information can be encoded into taggants of the invention in the form of resolvable excitation polarization angles. For example, if nanocrystals with polarized emissions (e.g. rods), are used in a taggant composition, then angles of polarization can be incorporated into the encoding scheme. The rods can be aligned, e.g., at predetermined angles (e.g., by brushing a nanorod paint onto a surface) to provide unique (and/or separately detectable) combinations of emission polarization angles relative to the tag or object.

In another embodiment, information can be encoded in the incident angle of polarized excitation wavelengths required to excite certain nanocrystal subsets. If a nanocrystal taggant composition consists of nanocrystal spheres, the spheres can absorb the excitation light from any direction, and the emission light can be non-polarized. However, a nanocrystal taggant composition of nanorods can be oriented, e.g., to be excited only by polarized excitation wavelengths incoming at an incident angle parallel to the rods. In this way subsets of nanorods with common orientation can be excited separately from nanorod subsets with other orientations. In the case, e.g., of polarization angle oriented nanocrystal rods, information can be sequentially gathered, e.g., by exciting the taggant composition from a first angle and detecting emissions from a first subset of oriented rods (the emissions typically returning in substantially in the opposite direction), then by exciting the taggant composition from another angle to excite a second subset of oriented rods to detect a second emission spectra. In this way, multiple encoded data sets can be detected from a single taggant composition.

Multi-dimensional encoding and decoding can be practiced using the compositions of the invention. For example, multiplexed data can be embedded in unique combinations of excitation wavelengths, excitation polarization angles, emission frequencies, emission frequency combinations, emission shapes, emission polarization angles, emission intensities, and/or emission spectral widths. The multiplexed data can be interpreted (deconvoluted) according algorithms adapted to each particular application. Computers and suitable software can be useful in interpretation of such multiplexed data encoded signals.

Adherent Matrices

Nanocrystals can be associated with adherent matrices in the compositions of the invention to facilitate tagging of objects. Such matrices can be, e.g., fluid matrices, adhesives, solid supports, sheet substrates, and/or the like.

In accordance with the present invention, the taggant composition typically also includes an adherent matrix that permits the affixation or admixture of the nanocrystals to objects (e.g., articles or materials) to be monitored. Such adherent matrices can be amorphous, e.g., gel like or liquid in composition, allowing fluidic application (tagging) of the composition, e.g., through spraying, injecting, brushing, inscribing, stamping, blending, wiping, applying, or painting of the taggant, into or onto the object. Alternatively, the adherent matrix can include or be coupled to (e.g., coated onto) a solid substrate such as, e.g., a glass, a crystal, an organic material, an inorganic material, a tape, a powder, a fiber, a decal, pin, clip, label, and/or the like, that allows affixation of the composition to a solid object by mounting, depositing, sticking, pinning, and the like. In one embodiment, a chemical linker group can act as an adherent matrix tagging one or more nanocrystal to, e.g., a biomolecule.

In one embodiment for shaped, patterned or indelible tagging, the adherent matrix can be a carrier or penetrant to facilitate incorporation of the taggant compound into the surface of an object to be monitored. For example, nanocrystals can be suspended in an adherent matrix of a solvent capable of penetrating the surface of the object. Exemplary solvents include liquids, such as, e.g., water, acetone, dimethylsulfoxone, alcohols, hydrocarbons, acids, alkalines, inks, surfactants, and/or the like. Tagging the object with carrier/penetrant taggant compositions can entail, e.g., inscribing, printing, or stamping the composition onto the object surface. Optionally, the taggant composition can comprise a pattern on the object surface visibly observable as a pigment incorporated into the composition or by instrumentation capable of detecting and displaying the nanocrystal emissions as an informative pattern.

The compositions of the invention can optionally include a matrix that facilitates their use as a taggant in particular applications. For example, in the case of taggants applied to the surface of articles or animals, the compositions typically include an adherent matrix or applicable support substrate, e.g., a tape or patch, for adhering the nanocrystal portion of the composition to the article or subject that is being monitored. Such adherent matrices can take a variety of forms. For example, they can comprise any of a variety of polymer matrices, e.g., plastic, latex, silicone, PEG, or any other curable polymer material that can be applied as a liquid composition with a suspension of nanocrystals and subsequently dried or cured in place to immobilize the nanocrystal component. The matrix can optionally comprise an adhesive in addition to the nanocrystal component, and be applied to one side of a transparent or translucent substrate, e.g., glass or plastic tape, so that the tape may be affixed to the article or subject that is too be monitored. In another particular embodiment, the nanocrystal composition can include, e.g., a substantially biocompatible solid support in the form of a pellet or beads that can be permanently positioned under the skin to tag an animal.

In some embodiments of the invention, the nanocrystals of the composition are, e.g., suspended in a solution suitable for administration to a mammal. For example, in embodiments where nanocrystals are employed in medical imaging, linked to bioactive agents, or intended for deposition inside animal tissues, nanocrystals can be formulated in compositions suitable for injection. Compositions of the invention can be administered to a mammal by delivering the bioactive material, e.g., through the intravenous, intramuscular, intraperitoneal, intracerebrospinal, subcutaneous, intra-articular, intrasynovial, intrathecal, oral, topical, intranasal, or pulmonary routes. Suitable preparations can contain, e.g., no components which are toxic to the animals to which the composition would be administered. Excipients, such as salts, sugars, buffers, polymers, can be part of the composition, e.g., to provide bulk, stability, and/or comfort on injection. Preferably, the excipients have been designated by the Federal Drug Administration (FDA) as 'Generally Regarded as Safe' (GRAS).

Methods of Monitoring Objects

Methods of the invention for monitoring objects include, e.g., tagging the object with a nanocrystal composition of the invention, exciting the nanocrystals on the tagged object with an appropriate excitation wavelength, and detecting the unique emission wavelengths emitted from the composition. The objects can be, e.g., any of a wide variety of suitable articles or materials. Tagging can be, e.g., by application onto or incorporation into the object. Exciting nanocrystals can be provided by illuminating with a spectrum of light ranging from ultraviolet light to infrared light, or the excitation light can be monochromatic, polychromatic, or broad-band. Detecting can include, e.g., receiving the nanocrystal emissions into a photo sensitive device with a display for technicians, or with data communications with a computer system.

As noted above, the methods of the invention can employ semiconductor nanocrystals that allow for the non-obtrusive monitoring of objects or materials. As used herein, non-obtrusive monitoring includes monitoring where one or more aspects of the monitoring operation are carried out without readily observable illumination from a light source and/or emissions from the object being monitored. For example, in monitoring of animals or other objects, e.g., products or materials, such monitoring would be substantially invisible to the monitored subject, or those observing the monitored object. Non-obtrusive monitoring also can include the monitoring of objects behind barriers, e.g., monitoring passage through the human body, for biological diagnostic applications, monitoring the movement of objects that are visibly obscured by living tissue, organic tissue, screens, vegetation, animals, smoke, clouds, rain, water, a fabric, a material that transmits nonvisible light, visibly obscured lines of sight and/or the like. As such, non-obtrusive monitoring also includes noninvasive monitoring methods, e.g., monitoring without requiring mechanical intrusion through a barrier, e.g., through skin or other barriers.

In a broad sense, non-obtrusive monitoring methods of the invention employ semiconductor nanocrystals in a tagging composition, where such nanocrystals, e.g., absorb and emit light outside of the visible spectrum, i.e., they absorb and emit in the non-visible range. In particular, nanocrystals are employed as the active portion of the tagging composition that absorb and emit in the UV range and/or the IR range of the spectrum. In practice, because of the red shift in the transition from absorption (excitation) to emission, the invention can provide nanocrystals that both absorb and emit in the UV range, absorb in the UV range and/or visible range and emit in the IR range, or both absorb and emit in the IR range. As used herein, the UV range is defined as between about 100 nm and about 400 nm, while the IR range is defined as between about 750 nm and less than about 500 um (including the near IR at between 700 nm and 1300 nm).

By utilizing a tagging composition that has an excitation spectrum that includes a nonvisible portion, one can utilize a light source at the nonvisible wavelength to illuminate the target object without such illumination being readily observable. Such non-obtrusive illumination is particularly useful in situations where clandestine monitoring is desired, e.g., in retail security or monitoring of animal movements, or in situations where extraneous illumination is otherwise not aesthetically desirable or could be potentially hazardous, e.g., in traffic monitoring, automatic toll booths, etc. In terms of absorption spectra (excitation wavelengths), it is understood that nanocrystal absorption spectra can be relatively broad and absorb in the visible and nonvisible range. However, as long as the absorption spectrum has a non visible component, one can select excitation wavelengths in the nonvisible component to invisibly excite the nanocrystal.

Similarly, by utilizing nanocrystals that emit light in a nonvisible range as the active component of a tagging composition, resulting emissions from such tags can be unobservable to the monitored subject, or to an individual observing the tagged object. Such invisible tags allow monitoring of materials where visible taggants would be aesthetically inappropriate, or otherwise deleterious to the functionality of the taggant or the material upon which the taggant is disposed.

Providing a Taggant Composition

Taggant compositions of the method include, e.g., nanocrystals with predetermined excitation and emissions spectra in combination with an adherent matrix or solution suitable for administration, as described in the Compositions of the Invention section above. The nanocrystals can be, e.g., tuned in the manufacturing processes to provide desired characteristics, such as particular excitation spectra, excitation polarity angles, emission polarity angles, emission spectra, emission spectral width, and/or emission intensity. Nanocrystal preparations can be, e.g., a mixture of subsets with information laden excitation combinations, emission combinations, polarization combinations, and/or emission intensity combinations. Nanocrystals can be, e.g., provided with useful coatings, and/or with chemical linkages to desired supports, bioactive molecules, members of molecular libraries, solubilizing chemical groups, insulating molecules, and/or the like.

Nanocrystals of the methods can be manufactured in various shapes and sizes. For example, nanocrystals can be nanosheets, nanowires, branched nanowires, or nanodots. Nanosheets can have a thickness, e.g., less than the Bohr radius for the particular crystal (generally, e.g., between about 0.1 nm and about 15 nm in thickness). Nanosheets can be fabricated, e.g., by self assembly of a monolayer or by vapor deposition onto a substrate. Nanocrystals can be heterogeneous structures, e.g., a core-shell, longitudinal heterostructure, or core-branch heterostructure. More typically, in the present invention, nanocrystals are nanoscale rods or dots of semiconductor material which can be manufactured by, e.g., photolithography and deposition, precipitating reactions in a coordinating solvent, or vapor deposition to seeded semiconductors, as sited above in the Nanocrystals section.

Optionally, nanocrystals of the methods can have surfaces populated with desirable chemical and/or binding groups, e.g., by linker reaction chemistries. Specific affinity molecules can be bound to the surface of nanocrystals through the use of linker chemistries. For example, dopants, substrate molecules, or applied coatings can provide linker reactive groups, such as amines, sulfhydryls, carboxylic acids, alcohols, aldehydes, and thiols, that can covalently bond to commercially available bivalent linker molecules. Binding groups can be cross-linked to nanocrystals using linkage chemistries including bivalent linker chains having terminal hydroxysuccinimide (reactive with primary amines), maleimides, haloacetyls, pyridyl disulfides (reactive with sulfhydryl groups), hydrazines (reactive with aldehydes), ethyldiethylamino propylcarbodiimide (EDC, reactive with carboxyl groups). Nanocrystals can be passivated by coating the semiconductor surface with a surfactant, e.g., tri-octyl phosphine (TOP) to reduce interference ionic reactions with the crystal. Hydrophobic insulating layers and hydrophilic solubilizing layers can be incorporated onto nanocrystals.

Figure 1B:
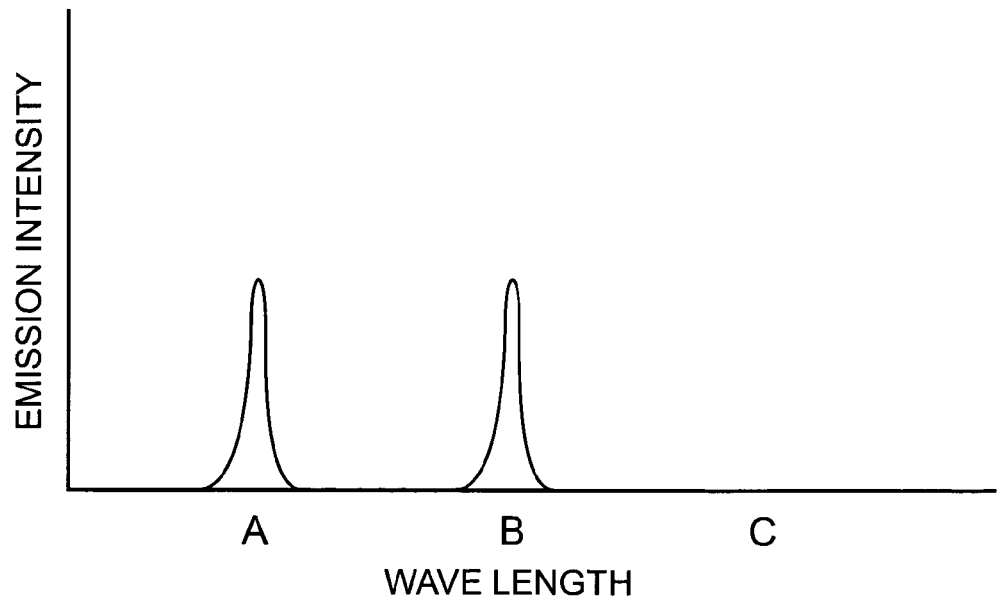

The compositions of the methods can comprise mixtures of two or more nanocrystal population subsets having different absorption and emission spectra to provide an expansive spectral encoding mechanism. In particular, spectrally different compositions can be mixed together in different combinations to provide a composition that is readily identifiable and distinguishable from other compositions. By way of example, three different nanocrystal populations, e.g., having three different emission spectra, can be combined to provide a first encoding mixture. A second encoding mixture can then be produced by substituting at least one of the nanocrystal populations in the first encoding mixture with a nanocrystal population that has yet another different emission spectrum. One can substitute one, two, or all of the nanocrystal populations to provide a distinguishable coding composition. For example, a first encoded composition can have nanocrystal subset with emissions at wavelength A and a second subset with emissions at wavelength C, as shown in FIG. 1A. The emission spectrum of a second composition with nanocrystal subsets with emissions at wavelengths A and B, as shown in FIG. 1B, can be readily distinguishable from the emission spectrum of the first composition.

Figure 2A:
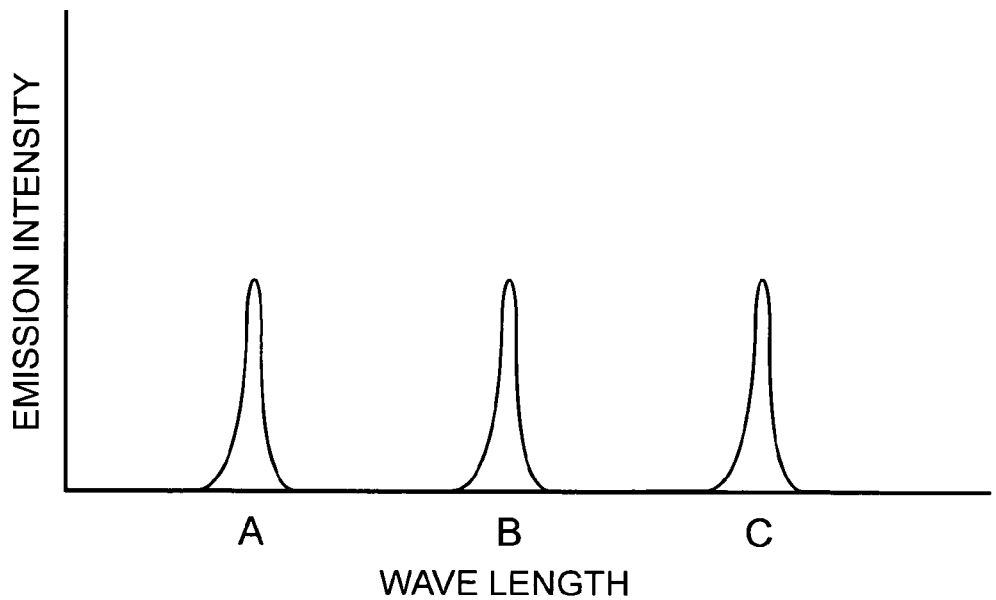
FIG. 2 is a schematic diagram of unique emission intensity combinations that can be encoded by nanocrystal subsets in a taggant composition.
Figure 2B:
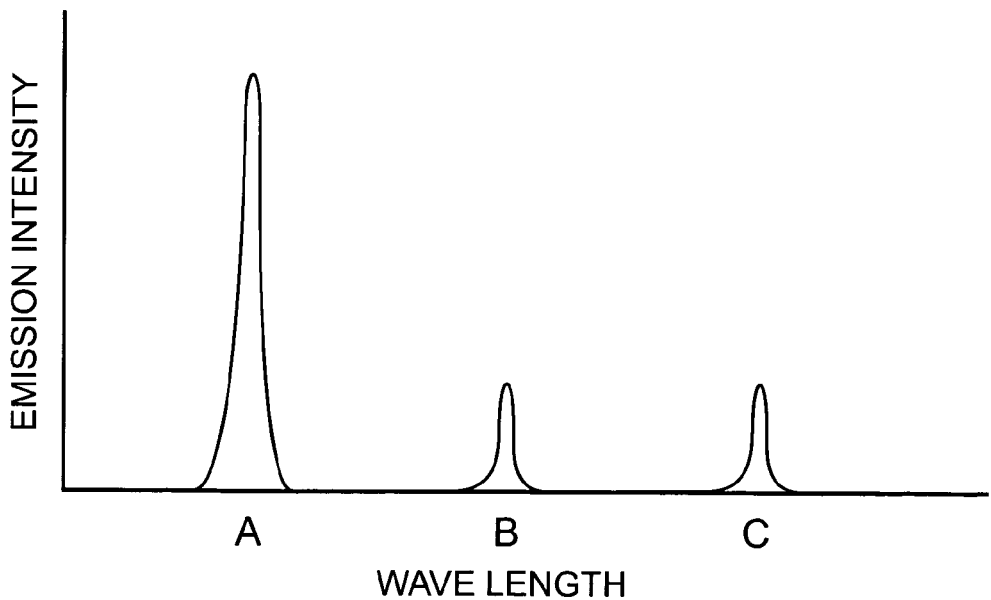

Further, one can adjust the relative concentrations of each different nanocrystal population subset (or otherwise tune subset emission intensities) to further provide a basis for distinguishing among encoding compositions. In particular, one can provide two encoding compositions that contain the same subsets of nanocrystals, but having different predetermined proportional representation of the subsets to provide distinguishable emission spectra between the compositions. By way of example, a first encoding composition can include nanocrystals that have emission spectra about wavelengths A, B and C at equal concentrations (e.g., 1 part A, 1 part B, 1 part C, as shown in FIG. 2A) to yield signals in those spectra at comparable intensity. By adjusting the relative proportions of the nanocrystal subsets (e.g., 2 parts A, 0.5 parts B and 0.5 parts C, as shown in FIG. 2B), one can provide a detectable and decodable difference in the emission spectra between the first and second compositions, as shown in FIGS. 2A and 2B.

Figure 3A:
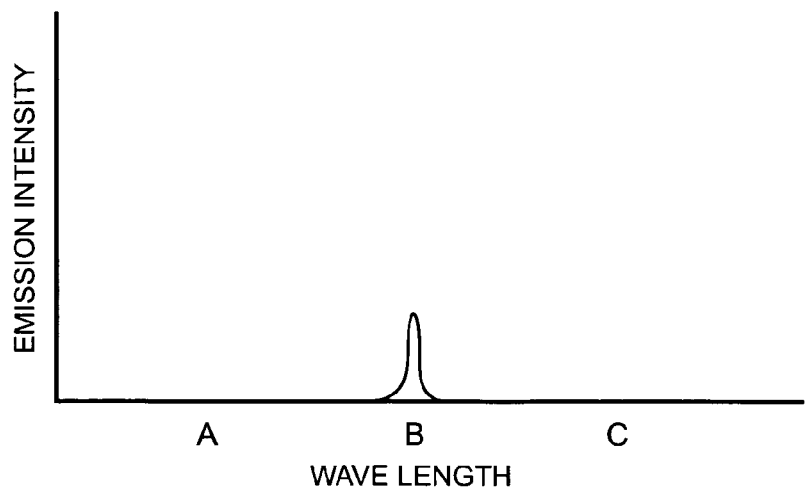
FIG. 3 is a schematic diagram of emission spectra for nanocrystal subsets having different excitation wavelengths and the same emission wavelength.
Figure 3B:
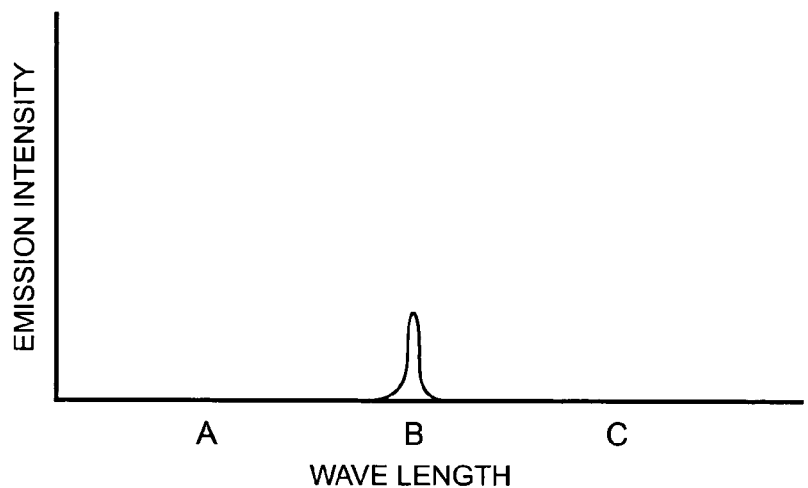
Figure 3C:
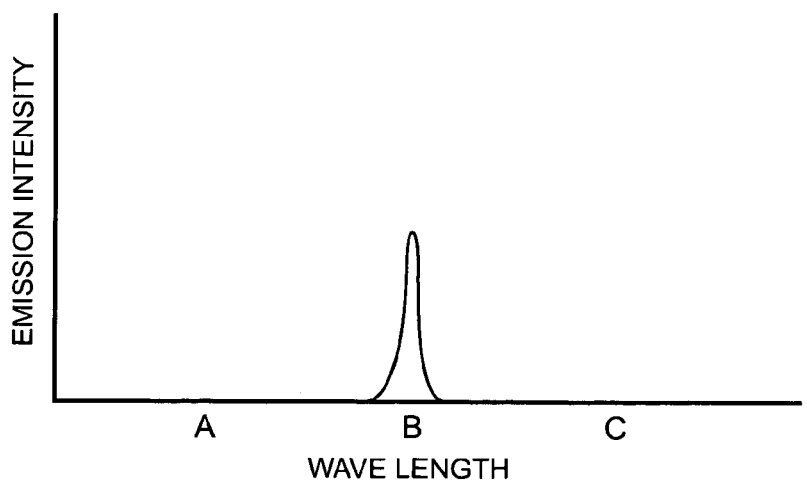
Figure 4A:
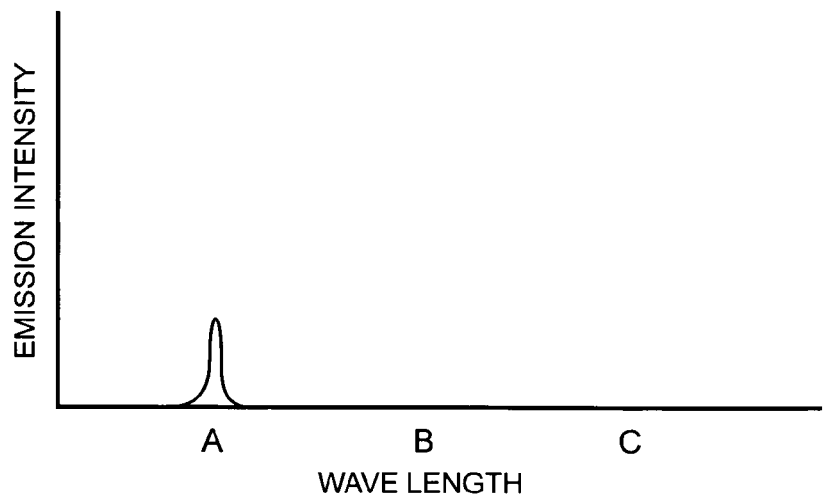
FIG. 4 is a schematic diagram of emission combinations for a nanocrystal population having nanocrystal subsets with different excitation wavelengths and different emission wavelengths.
Figure 4B:
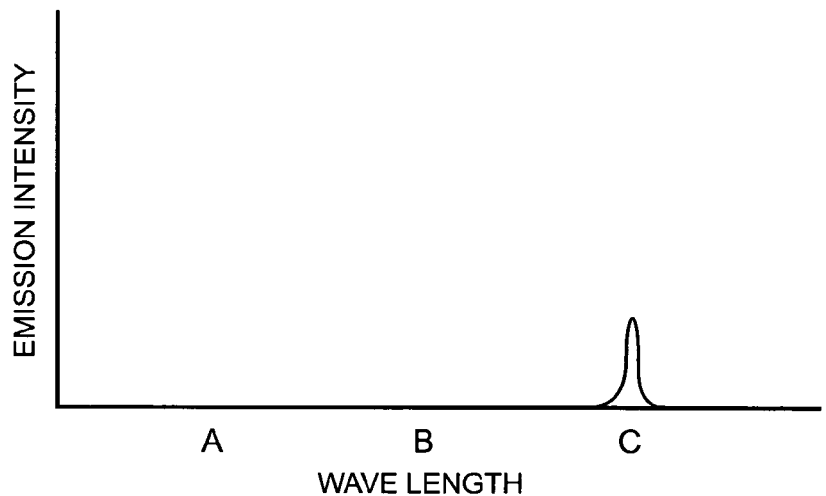
Figure 4C:
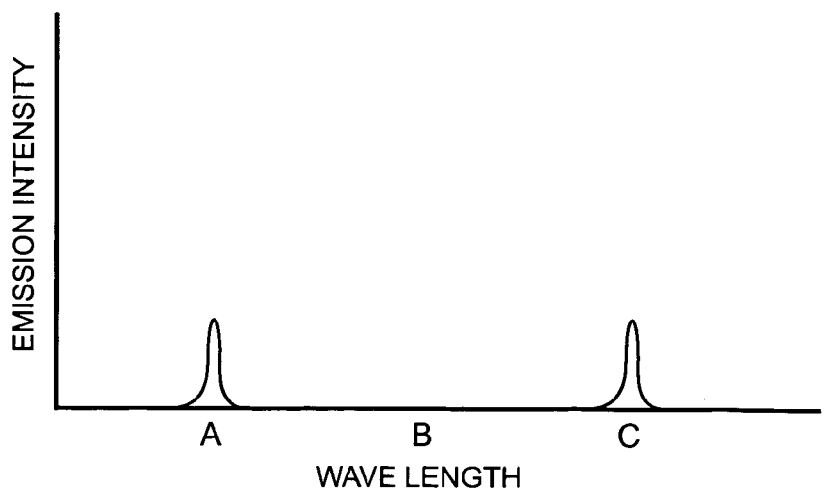

Unique encoding possibilities are presented by selection of excitation wavelengths used to illuminate compositions in the methods of the inventions. It is an aspect of the invention that compositions with different excitation wavelengths but the same emission wavelengths can be distinguished. Nanocrystal subsets with different predetermined excitation wavelengths can be separately, or jointly, excited to provide emissions bearing information. For example, a first nanocrystal subset can be excited by a UV wavelength and emit at IR wavelength B (as shown in FIG. 3A), while a second nanocrystal subset can be excited by a IR wavelength and also emit at IR wavelength B (as shown in FIG. 3B). When a mixed composition of the first and second nanocrystal subsets is illuminated with both the UV and IR excitation wavelengths, the resultant emissions can be a more intense at the emission wavelength (as shown in FIG. 3C). In another embodiment of encoding and decoding by selective excitation, the composition can include, e.g., nanocrystal subsets that excite at different wavelengths and emit at different wavelengths. For example, a first nanocrystal subset can be excited by a UV wavelength and emit at IR wavelength $\lambda$ (as shown in FIG. 4A), while a second nanocrystal subset can be excited by a IR wavelength but emit at IR wavelength C (as shown in FIG. 4B). When a mixed composition of the first and second nanocrystal subsets is illuminated with both the UV and IR excitation wavelengths, the resultant emission spectra can include both emission wavelengths (as shown in FIG. 4C). Although these examples describe the use of UV and IR excitation wavelengths, the scheme of excitation wavelength control can function using excitation wavelengths within the UV, visible, or IR spectra by choosing excitation wavelengths that do not significantly overlap between the particular nanocrystal subsets. A similar selective excitation scheme can be provided by using excitation angle polarized nanocrystal subsets, as is described below.

Encoding possibilities are presented by orientation of excitation/emission polarized nanocrystals in the compositions of the invention. For example, rod shaped nanocrystals with polarized excitation angles and/or emissions angles can be oriented, by mechanical brushing, combing, fluid flows, rolling, magnetic forces, directed crystal growth, manipulation of a matrix supporting the nanocrystals, and/or the like. In one embodiment, a population of polarized nanorods can be oriented, e.g., 90 degrees from the plane of a supporting substrate and another population can be oriented at 45 degrees from the plane of the substrate. In one aspect, the tagged substrate can be illuminated with a nonpolarized excitation light and polarized emission wavelengths can be detected separately from a detector located at a position 90 degrees from the plane of the substrate and (sequentially or concurrently) from a detector located at a position 45 degrees from the plane of the substrate.

Figure 5A:
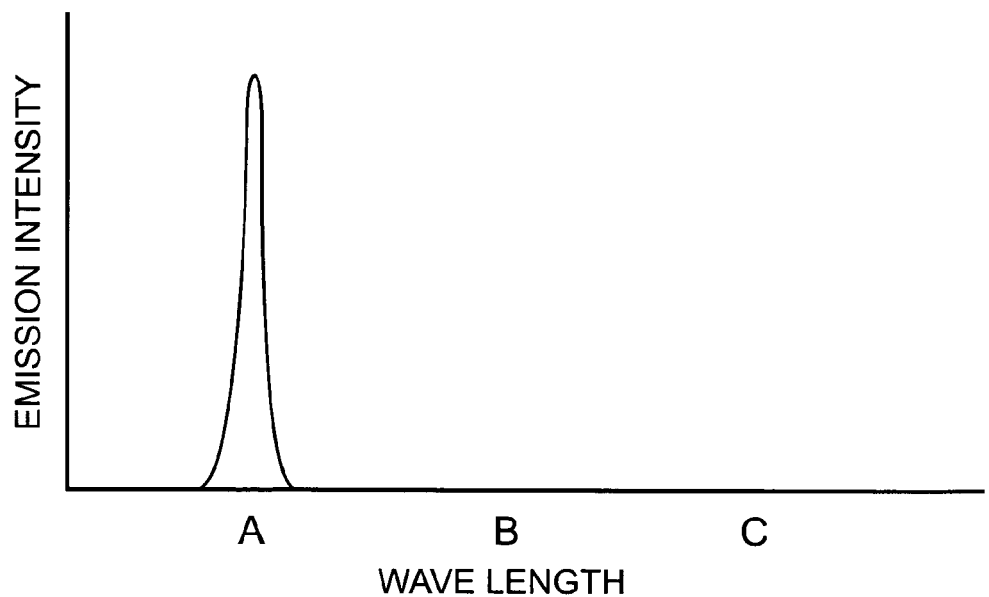
FIG. 5 is a schematic diagram of emission combinations for a nanocrystal population having nanocrystal subsets with different excitation wavelengths, different emission wavelengths, and different emission intensities.
Figure 5B:
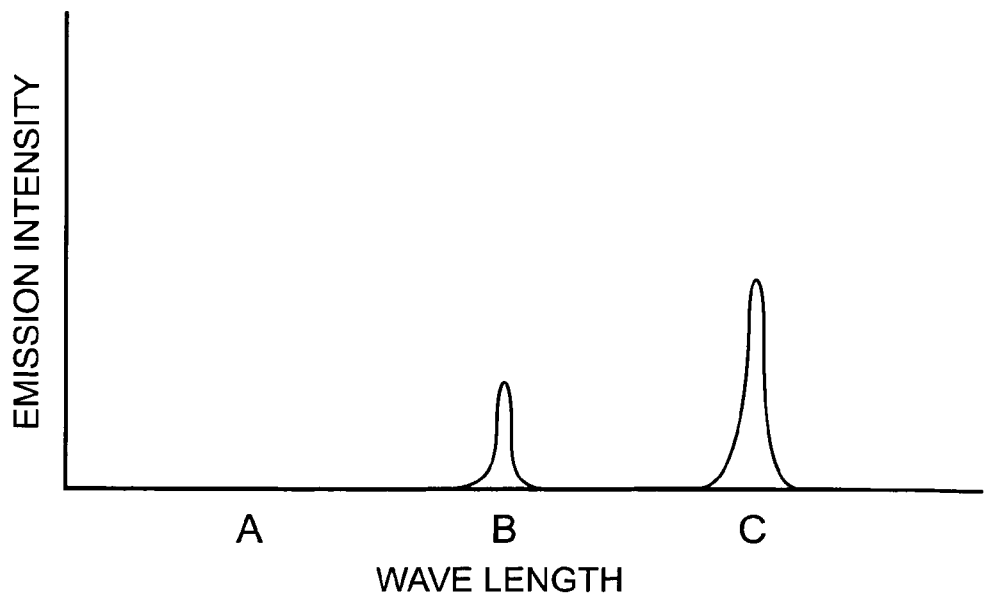

By encoding a composition with nanocrystal subsets having a combination of predetermined emission wavelengths, polarization angles, intensities, and/or excitation wavelengths, more data can be encoded in a smaller number of nanocrystal subsets. For example, a composition can be prepared from a first nanocrystal subset emitting at a wavelength of A at a strength of 2 intensity units on excitation with UV light, a second nanocrystal subset emitting at a wavelength of B at a strength of 0.5 intensity units on excitation with IR light, and a third nanocrystal subset emitting at a wavelength of C at a strength of 1 intensity unit on excitation with IR light. The composition can emit a spectra, as shown in FIG. 5A on illumination with IR light, and as shown in FIG. 5B on illumination with UV light. Even with this simple exemplary system the present invention is capable of encoding at least 144 unique emission patterns (8 emission wave length combinations×9 intensity combinations×2 excitation wavelengths). With each additional allowed emission wavelength, intensity, or excitation wavelength, the possible coding combinations can increase exponentially to provide unique identifiers for substantially any group of objects. Furthermore, a second set of polarized nanocrystals can be provided, e.g., with excitation illumination and/or emission detection from a particular angle to provide separately readable coding on the same tagged object.

The foregoing examples are illustrative of encoding mechanisms, and are not provided as complete examples. It will be appreciated by one of ordinary skill in the art that larger or smaller numbers of nanocrystal population subsets having more or fewer emission (and/or absorption) spectra may be employed in conjunction with adjustments in relative concentration in order to provide encoding mechanisms. One skilled in the art will appreciate the exponential marginal increase in possible data representation with each additional nanocrystal subset, intensity, bandwidth, polarization, or excitation wavelength in a taggant composition. In addition, further manipulations can be employed to provide further bases for distinction, such as e.g., applying the compositions in different conformations, e.g., as inscribed brands or marks, applying them to different positions, incorporating polarizing filters, or specific wavelength filters, etc.

Taggant compositions can be provided in a matrix appropriate to the particular object monitoring method to be practiced. Nanocrystals can exist as a powder that is dispersible and/or capable of deposition in or on objects. Nanocrystals can be suspended or dissolved in fluid matrices for tagging objects by application, injection, adhesion, penetration by capillary action, inscription, and/or the like. Nanocrystals can be incorporated into or onto solid substrates for tagging, e.g., by mechanical or adhesive attachment to the objects.

Methods of tagging objects with taggant compositions of the invention can include, e.g., application of taggant in visible or nonvisible topological or geometric (shape or pattern) identifiers. For example, the composition can be associated with a substrate or adherent matrix in the form of a tag with a unique shape, pattern, color, or symbol, that can visibly convey additional information. In one embodiment, a heart shape painted onto an object using a composition of nanocrystals can be distinguished, e.g., by an observer or a computerized video sensor, that from a circle-shaped nanocrystal tag. In another embodiment, livestock can be, e.g., tattooed with a particular near-IR tag that contains nanocrystal of only one subset, and the animals could be identified simply by the shape of the tattoo. In another aspect, taggant compositions can be applied in a manner that produces a unique pattern ("fingerprint") such as can occur when a fluid composition is injected into animal tissues or smeared onto a surface.

Methods of Tagging

Objects can be tagged with taggant compositions by physically associating the composition with the object in a suitable fashion. The choice of tagging method can depend on the nature of the object, the choice of excitation or emission wavelengths, the limitations of the monitoring system hardware, and the like. Objects for monitoring can be any solid or liquid matter of interest to be detected, identified, and/or tracked. Tagging can be by, e.g., surface application, mechanical mounting, or incorporation, as appropriate for the object/taggant combination.

Methods of the invention can tag a wide variety of objects, such as, e.g., solid articles, raw materials, analytical solutions, medical devices, and the like. Objects taggable by compositions, methods and systems of the invention can be, e.g., any solid or liquid material capable of permanently or temporarily receiving nanocrystal taggants. Solid article objects can include, e.g., retail items, manufactured goods, animals, vehicles, and the like. Raw material objects can include, e.g., chemicals, grains, powders, process intermediates, solutions, and the like. Analytical solution objects can be tagged with compositions of the invention for monitoring; such solutions can include, e.g., microfluidic samples or buffers, molecular libraries, biomolecules, and the like. Medical and veterinary devices are objects that can employ nanocrystal taggants, for example, in medical imaging injectables, subcutaneous identification tags, body fluid tracking "dyes", and the like.

The nanocrystals of the invention can be, e.g., powder particles that can tag objects by dusting onto a surface or mixing into a liquid or particulate material. For example, an object with a porous or textured surface can receive nanocrystal powder particles into depressions where they can settle for temporary or permanent tagging of the object. Where the object is a material, such as a liquid, slurry, gel, powder, grain, or mixable commodity, nanocrystals can be blended into the object to accomplish tagging. To accommodate spraying or mixing, in some circumstances, the nanocrystals can be blended with a liquid matrix, such as water or organic solvents before blending or application to porous objects.

Nanocrystal compositions of the methods can include a fluid adherent matrix, e.g., to facilitate application to certain objects. Adherent matrices can be, e.g., adhesive compositions for sticking nanocrystal taggants to objects. Such adhesives can be sticky hydrophilic polymers (starches, sugars, proteins, latex, etc.) or hydrophobic polymers (tars, resins, etc.). Fluid adherent matrices can be, e.g., applied in the form of an ink or paint for covering a surface of an object or marking a surface in a pattern. Optionally, fluid adherent matrices can include a visible pigment for ready location of the mark for scanning of emissions or to provide a visibly readable pattern with the tag.

Adherent matrices for nanocrystal tags can be, e.g., solid substrates. Nanocrystals can be applied to a surface of a solid substrate and/or incorporated into a solid substrate for labeling of objects. Exemplary solid supports can include tapes, buttons, labels, decals, ribbons, stickers, beads, appliqués, capsules, and the like. In one embodiment, the nanocrystal taggants are painted onto the surface of a button that is attached to an object with a pin. In another embodiment, nanocrystal taggants are applied to the back of a clear (substantially transparent to excitation and emission wavelengths) plastic decal and stuck onto the object. In still other embodiments, nanocrystal taggants are incorporated into capsules for insertion under the skin of an animal. In a particular embodiment, nanocrystals are linked to solid support beads used in "split and pool" molecular library synthesis. Tagging of objects using solid substrate adherent matrices can be by, e.g., chemical linkage (such as, e.g., gluing, cross linking, vaporizing and deposition, etc.), or mechanical linkage (such as, e.g., pinning, sticking, clipping, sewing, tying, bolting, hanging, etc.).

In some embodiments, cumulative tagging can be an aspect of the methods. For example, additional nanocrystal subsets can be tagged to the object over time. Such cumulative tagging can, e.g., allow updating the status of an object or provide a decodable history of events the object has experienced. In one embodiment, additional nanocrystals can be added, e.g., to a reaction mixture during each step of a synthetic process in order to keep track of a synthetic route employed to provide molecules found to be of interest.

Excitation of Nanocrystal Tags

Excitation of nanocrystals can be, e.g., by illumination with light having a shorter wavelength than the nanocrystal emission wavelength. The illumination can be general or directed. Particular excitation wavelengths can be selected, e.g., to penetrate obscuring barriers, or to allow selective scanning of certain nanocrystal subsets.

Fluorescence is the absorption of light at an excitation wavelength followed by emission of light at a longer wavelength. In methods of the invention, tagged objects can be scanned by illuminating the tag with an excitation wavelength and detecting emission at a longer wavelength. Illumination can be by general dispersal of excitation wavelengths in the environment of the tagged object or by directed illumination using optics to target the tag. An illumination light source can provide a broad spectrum of light or essentially monochromatic light.

Light sources for excitation wavelengths can be any, known in the art, that can provide the desired UV, visible, and/or IR light. Light sources can be, e.g., mercury vapor lamps, metal halide lamps, incandescent lamps, deuterium lamps, electric arcs, lasers, flames, light emitting diodes, fluorescent tubes, cathode tubes, noble gas lamps, light emitting diodes, the sun, fluorescence from other molecules in the composition, and/or the like. Light sources can generally disperse light, or the light can be channeled through optics and/or monochromometers for selected and directed excitation wavelengths. In many embodiments, it is preferred that the illuminating light source not provide significant light at emission wavelengths in order to reduce background during detection of emission signals.

Optics can be used, e.g., to direct and adjust light from a light source before illumination of nanocrystal tags. Source light can be directed, e.g., using standard optical devices, such as mirrors, apertures, and lenses. Optical direction of excitation light can allow scanning without movement of the light source, concentration of light energy on the tag, and/or reduced escape of hazardous wavelengths into the environment of living organisms. Light spectra from a source can be adjusted to provide the desired wavelengths by transmission through wavelength filters, polarizing filters, prisms, gratings, and/or the like. Many useful excitation wavelengths of monochromatic light can be obtained from lasers or light emitting diodes.

Monochromatic light, or light restricted to particular spectrums, can be useful in embodiments where nanocrystal encoding includes alternate excitation wavelengths, as previously discussed in the Providing a Taggant Composition section above and as shown in FIG. 4. Where the alternate excitation wavelengths are broadly separated, such as when one wavelength is UV and the other IR, alternate illumination can be supplied by separate light sources, such as a heat filtered xenon lamp and an incandescent lamp. Where the alternate excitation wavelengths are closer together, suitable illumination can be provided by narrow spectrum sources such as selectively defracted light, filtered light, or lasers. Provision can be made to supply the alternate excitation wavelengths for illumination at separate times or at once, as will be apparent to those skilled in the art. Polarized light can be provided by lasers, polarized optical filters, LEDs, and the like.

In embodiments of the methods where tags are scanned through obscured lines of sight (barriers), preferred excitation wavelengths can be, e.g., infrared wavelengths, more preferably, near infrared wavelengths. Longer wavelengths are known to be attenuated to a lesser degree by barriers than shorter wavelengths. Because of its high penetration ability, infrared light has been used by the military to view battlefields through smoke and by doctors to actuate anticancer drugs through human tissue in photodynamic therapy regimens. In the present invention, infrared light can be used to provide an advantage in illuminating nanocrystal tags through obscuring barriers, such as, e.g., smoke, clutter, living tissues, organic tissue, vegetation, dust, fabrics, foliage, glass, plastics, animals, rain, screens, turbidity, clouds, and the like. Infrared wavelengths for methods of illuminating through barriers in the invention can range, e.g., from about 700 nm to about 1 mm, less than about 40,000 nm, less than about 5,000 nm, less than about 3500 nm, less than about 1700 nm, less than about 1300 nm or less than about 900 nm. Excitation wavelengths ranging from about 1300 nm to about 650 nm are preferred for illumination of tagged objects through barriers.

Detection of Invisible Nanocrystal Tag Emissions

After absorption of excitation wavelengths by nanocrystals of the invention, part of the energy can be emitted as longer, invisible wavelengths. Detection of these emission wavelengths can signal the presence, identity, and/or location of tagged objects. Emission wavelengths can be selected, e.g., for invisibility and/or detection of tagged objects through obscuring barriers.

Invisible emission wavelengths from nanocrystal compositions of the invention can be, e.g., in the ultraviolet and/or the infrared spectra. Detection of the emissions can be by detectors, such as, e.g., a fluorometer, a spectrophotometer, a photomultiplier tube, a photodiode, a CCD, a CMOS sensor, an eye, or a diode array, and the like. Light received by the detector can be modified, e.g., to enhance selectivity and/or sensitivity of detection. For example, optical systems (e.g., comprising lenses, mirrors, and/or apertures) can be used to restrict reception to only light originating in a particular direction. In another example, detectors can screen out light (e.g., using filters, prisms, defraction gratings, and/or specifically sensitive photodiodes) to reduce background noise from visible and non-emission wavelengths.

In embodiments of the methods where tags are scanned through obscured lines of sight, preferred emission wavelengths can be, e.g., infrared wavelengths, including near IR wavelengths (as with excitation wavelengths, discussed above). In the present invention, infrared light can be used to provide an advantage in detecting nanocrystal tags through obscuring barriers, such as, e.g., smoke, clutter, living tissues, dust, fabrics, screens, plastics, rain, animals, foliage, glass, plastics, screens, turbidity, clouds, and the like. Infrared emission wavelengths for methods of detecting tagged objects through barriers in the invention can range, e.g., from about 700 nm to about 1 mm, less than about 40,000 nm, less than about 5,000 nm, less than about 3500 nm, less than about 1700 nm, less than about 1300 nm or less than about 900 nm. Emission wavelengths ranging from about 1300 nm to about 650 nm being preferred for detection of tagged objects through barriers.

Remote detection can be an aspect of the invention. In certain embodiments of the invention tagged objects can be remotely detected, e.g., when the tagged object is outside of the confines of the object monitoring system apparatus. For example, remote detection can include methods where the excitation light is projected to illuminate an external environment and any emitted light detected from an object of interest is received from the external environment. Remote detection can include, e.g., detection of objects that are not substantially between the light source and light detector, or detection of objects that are more than about 1 meter from the light source or light detector.

Automated detection can be an aspect of the invention methods. Automated detection can include, e.g., substantially continuous illumination of an environment and substantially continuous scanning of the environment until emission wavelengths of a predetermined code are detected (a detection event). Substantially continuous can include, e.g., continuous, punctuated, periodic or intermittent actions over a period of time. Automated detection can provide, e.g., detection of objects of interest which can appear in a monitored environment at unpredictable times. Such methods of automated detection can be useful, e.g., in monitoring of store exits for the presence of stolen goods, for toll booth monitoring, or for tracking and management of livestock on a ranch.

Detectors of the invention can provide, e.g., a simple analog or digital signal to an operator, or transfer a signal to a logic device (such as, a computer system) for interpretation, display, and/or data storage, as appropriate.

Decoding Taggant Emissions

Decoding detected taggant emissions signals can include, e.g., deconvolution of information encoded in an emissions pattern. Decoding can be as simple as, e.g., provision of an operator display in response to detection of an emission wavelength. Decoding can require evaluation of a complex combination of excitation wavelengths, excitation polarization angles, detected emission wavelengths, emission wavelength combinations, emission polarization angles, emissions spectral widths, emissions intensities, and the shape or pattern of the emitted light for interpretation by a logic device to determine presence, identity, and/or location of one or more objects.

The presence of an object tagged with a single subset of nanocrystals can result in a voltage change at a detector, such as a photomultiplier tube or photodiode sensitive to the emission wavelength. Decoding can be as simple as, e.g., sensing the existence of the emission (i.e., decoding of simple binary (yes/no) emission signals does not require deconvolution of emission combinations or multiplexed signals). In such a case, a logic device can be a volt meter that displays a voltage change to a system operator.

Decoding of emissions spectra can involve logical evaluation of multiple spectra characteristics encoded with information. An emission spectra can combine data transmission elements of, e.g., emission wavelength, emissions polarization, emission wavelength combinations, and emission intensities to provide a large number of unique combinations, as described in detail in the Providing a Taggant Composition section above. Additional dimensions of multiplexing can be added in embodiments where the emissions spectra vary depending on which predetermined excitation spectra or polarization is selected to illuminate the taggant composition. A simple detector and logic device can be sequentially adjusted to evaluate data transmission elements (e.g., excitation wavelength, emission frequency combinations, emissions wavelength, emissions spectral width, emissions intensity) of a taggant composition. However, the process of decoding complex emissions signals can be greatly facilitated, e.g., by a rapid scanning spectrophotometer communicating with a computer system adapted to deconvolute the multiplexed data to monitor tagged objects.

A computer system (logic device) for decoding emissions data can, e.g., receive detector signal input data, store data, deconvolute multiplexed signals, make calculations, direct excitation by alternate wavelengths, evaluate situations, and/or display messages. Systems in the present invention can include, e.g., a digital computer with data sets and instruction sets entered into a software system to practice the methods described herein. The computer can be, e.g., a PC (Intel x86 or Pentium chip-compatible with DOS®, OS2®, WINDOWS® operating systems) a MACINTOSH®, Power PC, or SUN® work station (compatible with a LINUX or UNIX operating system) or other commercially available computer which is known to one of skill. Software for interpretation of emission spectra is available, or can easily be constructed by one of skill using a standard programming language such as Visualbasic, Fortran, Basic, Java, or the like.

Authentication of Nanocrystal Taggant Emissions

As noted above, an emission spectra can combine data transmission elements of, e.g., emission wavelength, emissions polarization, emission wavelength combinations, and emission intensities to provide a large number of unique combinations, as described in detail in the Providing a Taggant Composition section above. While such a system can be used to create many different codes for tagging objects for inventory control, security monitoring, etc., its application to authentication and security inks is somewhat less robust since it is possible to replicate a code if a would-be-forger has access to the emission spectra of the item. The present invention thus also provides an authentication scheme that takes advantage of the unique emission and absorption characteristics of nanocrystals to create a spectral code that is far more difficult to decode and replicate than those previously employed.

It is well known that differences in the absorption spectrum from different sized nanocrystals in a mixture can result in changes in the relative intensity of the resulting emission from each different size as the excitation wavelength is changed. As an example, a mixture of red emitting and blue-emitting dots can both be excited with violet excitation light. If the excitation wavelength is shifted to the red or blue, however, the relative intensities of the red and blue emission will change do to the non-linear absorption spectra of the two dots. As such, it is necessary to use a specific excitation wavelength to ensure that the correct "code" is read.

A lesser-known characteristic of nanocrystals is that the emission wavelength of any particular nanocrystal is somewhat sensitive to the excitation wavelength. The reason for this is that each sample of nanocrystals comprises a distribution of sizes within it, and therefore by changing the excitation wavelength, different sub-populations of nanocrystals within the sample are excited, resulting in a shift of the peak wavelength. These shifts can be quite large (e.g., 10 nm or more) and are therefore easily detectable. This is another example of how the exact wavelength of the excitation can be critical in decoding the correct code. This has been addressed in the past by using broad-band excitation light, so that all nanocrystals in a given sample are equally excited, or by only using a single excitation wavelength for decoding so that the same populations of nanocrystals are excited every time.

The current embodiment of the present invention relates to a method of encoding and decoding nanocrystal spectral codes wherein a select, numeric excitation wavelength acts as part of the code. If an item is encoded using a specific excitation wavelength (e.g., 435 nm), that wavelength must also be provided to the person whom needs to decode the spectral code for it to be authenticated. If the code is measured by a third party without access to the excitation wavelength, the excitation wavelength will not be known, and therefore, the emission wavelength profile that is measured by the third party will be different than the expected emission wavelength profile for that code when measured with the correct excitation wavelength. If this "incorrect code" is then forged by combining nanocrystals in a mixture to replicate the spectrum under the incorrect excitation wavelength, the new code will not match the expected code when observed with the correct excitation wavelength. In this way, the excitation spectrum has become part of the code. Even in the situation where the third party observes the "correct" emission spectrum while it is being illuminated by an authorized person with the correct excitation wavelength, if the excitation wavelength is unknown to the third party, it will still not be possible to replicate a nanocrystal mixture that will be authenticated, since the composition of the mixture needed to produce the correct spectrum will depend on the excitation wavelength used to measure that spectrum. It is to be appreciated that the present embodiment of the invention can use changes in the wavelength or intensity of the emission spectrum. It can also use nanocrystals of different composition (and/or sizes) that can have the same emission spectrum but different excitation spectra and vice versa. The spectral code can rely on any one or more of the electromagnetic or fluorescent characteristics of the excitation light including, for example, the number of excitation peaks, relative excitation peak intensities, relative excitation peak wavelengths, absolute excitation peak wavelengths, excitation polarization angles, and overall excitation peak-shapes or patterns. Such spectral codes can be used, for example, for taggant applications and friend-or-foe identification, or for any other application where authentication of identity is important.

Systems for Monitoring Objects

Systems for unobtrusive monitoring of objects tagged with taggant compositions of the invention generally provide, e.g., a light source, and a light detector in communication with a logic device to determine the presence, identity, and/or location of the composition and associated object. The system can be configured to provide monitoring of many different objects in a wide variety of circumstances.

Taggant Compositions of the System

Fluorescent nanocrystal taggant compositions can have, e.g., unique excitation and/or emission wavelengths, and can be disposed in an adherent matrix to aid in tagging of an object. Taggant compositions of the systems for monitoring objects can be, e.g., any of the compositions previously described the Compositions of the Invention section above. In the system, taggant compositions can be tagged to objects of interest, e.g., as described in the Methods of Tagging section above.

Nanocrystals of the compositions can be, e.g., semiconductor nanocrystals such as, a nanodot, a nanorod, a branched nanorod, a nanocrystal, a coated nanocrystal, a passivated nanocrystal, or a derivitized nanocrystal. Nanocrystals of the system can provide a single emission frequency on excitation, or can be a mixed population of nanocrystal subsets providing a particular combination of excitation wavelengths, emission wavelengths, and/or emission intensities. Such crystals can be manufactured, e.g., by colloidal synthesis, precipitation, monolayer self assembly, photolithography, vapor deposition, VLS growth, gas-phase nucleation and growth, solution-phase nucleation and growth, and/or the like. The nanocrystals can be tuned to provide desired excitation wavelengths, excitation polarity angles, emission wavelengths, emission polarity angles, emissions intensities, and/or emission bandwidths by, e.g., controlling the size of the nanocrystals, size distribution, composition, mass percent of a constituent, or representation of a nanocrystal subset. The nanocrystals can, e.g., have excitation and/or emissions wavelengths in nonvisible light spectra, such as the UV and IR regions.

The composition of the system can include an adherent matrix, e.g., to aid in the tagging of the object. The adherent matrix can be, e.g., a polymer, glass, a crystal, an organic material, an inorganic material, a liquid, a penetrant, a solid support, tape, a patch, a capsule, a powder, a fiber, a decal, a pin, a clip, a label, ink, or an adhesive. Objects can be tagged with compositions of the invention by, e.g., depositing, spraying, brushing, taping, combining, mounting, injecting, blending, wiping, painting, inscribing, stamping, sticking, pinning, applying the composition into or onto the object, and/or by vapor deposition. Nanocrystals can be tagged onto objects with or without the aid of adherent matrices.

Light Source Configurations

Light sources, as described in detail above in the Excitation of Nanocrystal Tags section, can be adapted provide excitation wavelengths at the intensity, at the frequency, at the location, at the time, and/or in the bandwidth desired for a particular application. Light sources of the invention can include, e.g., mercury vapor lamps, metal halide lamps, incandescent lamps, deuterium lamps, electric arcs, lasers, flames, light emitting diodes, fluorescent tubes, cathode tubes, noble gas lamps, light emitting diodes, the sun, fluorescence from molecules within the composition, and/or the like. Depending on the circumstances, light sources of the monitoring systems can be configured to direct predetermined excitation wavelengths at a distant object (e.g., a vehicle) or a close up object (e.g., analyte molecules in a microfluidic channel). The light source can be required to provide alternate excitation wavelengths in a timed sequence of probing illuminations.

The wavelength and bandwidth of excitation light illumination can be controlled as described in the Methods of Monitoring Objects section above, and as is known by those skilled in the art. Excitation wavelengths can be selected for monitoring systems of the invention by the choice of light sources, and/or the use of optics such as filters, prisms and defraction gratings.

Light can radiate in three dimensions from a point light source to generally illuminate an environment to be monitored or the light can be directed. In situations where the object (such as, e.g., members of a molecular library in a random array, animals grazing in a field, or medical imaging of compositions in an organism) will not necessarily appear at a specific location, the general environment can be illuminated to cover all possible locations. In this configuration, the presence of a tagged object can be detected by a general detector scan of the environment. The location of the object can be determined using a detection scan with a directed focus. Light sources for general illumination are typically lamps, e.g., surrounded with an appropriate filter (to remove visible wavelengths or predetermined emission wavelengths). A reflector is commonly mounted to the back of the light source to redirect stray light onto monitored environments.

Alternately, the light source can be configured to focus illumination on to a particular location for monitoring tagged objects that are present or passing through the location. In such a case, the intensity of the light source can be lower than with general illumination, but optics, such as mirrors, apertures, and lenses can be required to direct the light to the location of interest. Directed illumination can optionally be provided by using laser light sources. In some embodiments, directed light can be provided to remote or relatively small locations using optic fibers, often in conjunction with light emitting diodes. Directed light sources can be useful in monitoring of locations, such as, e.g., a cashier's counter at a retail store, a traffic lane at a toll booth, or flow channels of a microfluidic device.

Light sources can be adapted to provide two or more specific excitation wavelengths at different times. In one embodiment, two wavelengths can be provided by two independent light sources, such as a heat lamp and a mercury vapor lamp. The lamps can be alternately energized (turned on) or their illumination alternately directed at the object by use of an optical shutter mechanism. In another embodiment, the one or more light sources can be directed through a variable monochromometer, such as a prism or defraction grating, to provide the selected excitation frequencies at the desired time. Optionally, illumination can be under the control of (or be detectable by) a computer system for coordination of excitation events with emissions detection for proper decoding of an excitation/emission sequence. Use of alternate excitation wavelengths can be beneficial, for example, where a very large number of objects require unique identification codes, or where it is desirable to separate objects into unique excitation classes.

Light Detectors

Light detectors, as described in detail above in the Detection of Invisible Nanocrystal Tag Emissions section above, can, e.g., receive and detect emission wavelengths at predetermined frequencies, determine intensity, at a desired location, at a required time, and/or with a bandwidth required for a particular application. The light detectors can be in communication with a logic device to interpret (i.e., decode, display, and/or store detection events) signals from the detector.

Light detector hardware can be any sensors and other hardware appropriate to receive the selected emission wavelengths under the circumstances of a particular embodiment of the invention. The detector can include, e.g., a light sensor in functional association with an optics system. For example, the light detector can comprise light sensor, a fluorometer, a spectrophotometer, a photomultiplier tube, a photodiode, a CCD, a CMOS sensor, a diode array, or the eye of an observer. Emissions from an object can be transmitted to the light sensor, e.g., by optics, such as lenses, mirrors, optic cables, and/or the like.

Light detectors can be, e.g., imaging systems, such as film cameras or digital cameras. Detection systems which include image detection can provide spatial information useful, e.g., in locating an object or interpreting shape or pattern information of a nanocrystal tag. A near-IR detecting camera or detector array (such as a near-IR hyperspectral imaging system) that can obtain intensity information, spectral information, and/or image information, is preferred in such embodiments.

Predetermined emission wavelengths can be selectively detected by any of a variety techniques known in the art. In an environment where there is little stray light, the simple presence of a tagged object can be detected by a sensor sensitive to broad spectrum of wavelengths (typically, a filter capable of removing the excitation wavelengths is placed in the detector light path). Many light sensors, such as photodiodes, can be inherently sensitive to only specific wavelengths of light. In a common configuration, the light sensor can be sensitive to a broad spectrum of emission wavelengths while selectivity is provided by an optics system comprising light filters, prisms, defraction gratings, and the like. In one embodiment, the light sensor is sensitive to a broad spectrum of light but the light detector can be configured to detect narrow emissions bands by adjusting monochromometer optics. Such detector systems can be capable of sequential detection of more than one emission wavelength. Optionally, the detector can include an array of photodiodes capable of detecting more than one emission wavelength at a time.

As with selection of particular emission wavelengths, as discussed above, the bandwidth of detectable emissions wavelengths can be configured, as appropriate for particular applications, according to techniques known in the art. Generally, the precision of wavelength selection can be increased to provide narrower detection band width. Narrow bandwidth can be particularly important, e.g., in applications where a large number of possible emission wavelength code combinations are required.

The intensity of emissions can be detected by many light detectors of the invention. For example, many photomultiplier tubes and photodiodes can transmit a signal (e.g., voltage or current) proportional to the intensity of light received. Such signals can be displayed on simple analog devices (such as a galvanometer) or converted to digital signals for manipulation by a digital computer. As received emission extensity can vary, e.g., with distance from the object or the presence of obstructions, a reference wavelength can be received for comparison and logical adjustment (normalization). For example, an internal reference nanocrystal tag or fluorescent molecule can be provided in the taggant composition on the object so that the relative intensity of wavelengths received from the object can be interpreted in decoding taggant nanocrystal intensity combinations.

The location of emissions can be determined precisely as required in particular embodiments of the invention. A light sensor can be generally exposed to light, e.g., from a broad area in embodiments where the presence of a tagged object anywhere in an environment is to be detected. In other embodiments, detection of emissions can be focused on a small area, e.g., through the use of optic elements, such as lenses, optic cables, mirrors, and/or the like. In some embodiments, emissions can be received from remote or relatively small locations using optic fibers, often in conjunction with photodiodes. Focused light detection can be useful in, e.g., monitoring a retail store exit, determining the location of a microarray library member, or monitoring flow channels of a microfluidic device.

The time of emissions detection can be important in some embodiments of the monitoring systems of the invention. For example, precise timing can be important in decoding of nanocrystal compositions with multiple excitation wavelengths or where the presence of an object at a particular time is important (such as during sequential analysis of labeled test samples, vehicles passing through a variable rate toll booth, or monitoring of animal behaviors). Time monitoring can be provided by a simple mechanical device, such as a moving chart paper. Typically, time monitoring is accomplished by digital storage of time associated excitation/emissions events in a computer system.

Logic Devices

Logic devices of the invention systems can be in communication with the light detectors of the system to provide a usable information output (interpret detector signals). The logic devices can be, e.g., simple analog devices such as a gage or meter. The logic devices can be, e.g., digital devices with simple (yes/no, on/off) signal displays or complex computer systems capable of instructing subsystems, collecting data, evaluating data, graphic displays, and storing data.

The output of a light detector is typically a variable electrical voltage. As the voltage is generally not detectable by a system operator, the detector output of a detection event is generally transmitted to a logic device for interpretation (e.g., decoding, determining appropriate displays to operators, and/or storing events). For example, the logic device can be a simple volt meter that changes readout (an appropriate display to an operator) in response to the voltage change. As the signal from nanocrystal compositions can be information rich, it is often beneficial to feed the detector signal to a computer system for interpretation.

Digital logic devices of the system can include, e.g., light emitting diodes, transistors, circuit boards, integrated circuits, central processing units, computer systems, computer networks, and/or the like. Computer systems can include, e.g., digital computer hardware with data sets and instruction sets entered into a software system. The computer can be in communication with the detector, signal a presence, identity or location of the composition to a system operator. The computer can be, e.g., a PC (Intel x86 or Pentium chip-compatible with DOS®, OS2®, WINDOWS® operating systems) a MACINTOSH®, Power PC, or SUN® work station (compatible with a LINUX or UNIX operating system) or other commercially available computer which is known to one of skill. Software for interpretation of emission spectra is available, or can easily be constructed by one of skill using a standard programming language such as Visualbasic, Fortran, Basic, Java, or the like. A computer system for decoding emissions data can, e.g., receive input data, store data, make calculations, and direct excitation by alternate wavelengths.

EXAMPLES

The following examples are offered to illustrate, but not to limit the claimed invention.

Tagging Retail Articles

In an example of tagging retail articles, an information rich composition is attached to the article as stick on labels for detection and identification on passing a check out counter scanner. Optionally, nanocrystal can be incorporated, e.g., directly into the material casing of an article by the manufacturer so that it can be detected from any direction and so it cannot be removed.

The taggant composition includes up to 6 different fluorescent nanocrystal types (subsets) that are mixed into an adherent matrix of acrylic polymer and sprayed onto the surface of the labels. The nanocrystal subsets are adjusted to provide information encoded with emissions unique in both wavelength and intensity. One of the nanocrystal subsets is a reference subset for comparison to determine at least 10 different relative intensity values for the 5 other subsets ($10^5$ coding combinations). The 5 coding nanocrystal subsets can be selected from a range of over 100 well resolved emission wavelengths in the mid IR spectrum for about 75,287,520 possible emission wavelength combinations. The composition on the retail labels is capable of encoding at least about $7.5 \times 10^{12}$ possible wavelength/intensity combinations. With a retail outlet carrying about 10,000 retail items, any reading (decoding) error will likely be discovered as an invalid (unassigned) number.

The exemplary system for monitoring retail items at the check stand is similar to bar code reading systems used in many high volume retail outlets. A near IR light source, filtered to remove mid IR wavelengths, is positioned beside the check out counter and directed to a location where a clerk handles the items. A light detector with a diode array is located next to the light source in communication with a central computer system. As retail items are illuminated by the light source, they give off a unique pattern of light emission wavelengths and intensities. The light detector diode array can simultaneously detect the intensity reference emission and resolve the 5 encoded emissions by intensity and wavelength. Wavelength information is passed directly to the central computer while intensity signals are converted to digital values by an A/D converter before computer input. The computer compares the reference intensity to the intensity of coding emissions for assignment of intensity values. The computer compares the received wavelength/intensity combination with a database of retail item identification numbers (combinations) to identify the item. The computer database provides information, such as an associated item name and price, and signals the retail clerk through a digital display screen. The computer can update an inventory database to provide near real time data for marketing, productivity evaluation, and just in time shipping decisions. Periodic inventories of items on the shelf can be obtained using hand held scanners.

This exemplary retail monitoring system can have several advantages over bar coding systems. For example, the nanocrystal emissions can be read as a combination instead of as a bar code sequence (permutation); therefore, reading does not require motion of the tagged object or light source. With nanocrystal taggants of the invention, the retail clerk simply places the retail item in the presence of the light source and detector without the need to swipe the label past the detector. While bar code readers commonly use laser lights and complex optics systems to provide a scanning light source, the present invention can employ general illumination with a simple lamp, such as an incandescent light bulb. Because the excitation and emissions wavelengths can be invisible, the light source and label can be less apparent than with a bar code system. This nonobtrusive aspect can be employed in theft prevention, for example, by comparing item combinations in a cart leaving the store to recent known purchase combinations.

Security

Taggant compositions of the invention can have significant advantages in security applications. Clothing retailers can detect and prevent thefts, for example, by labeling clothes with nanocrystal taggants.

In one example, clothing items are dusted with a nanocrystal composition for detection at exit doors. The security label nanocrystals are present in a simple subset combination that can not be confused with nonspecific light sources or fluorescent emissions of common items. The nanocrystal subset combination is unique to the store so that items from other retailers do not produce not false positives in the security system. The nanocrystals are spayed onto clothing for sale with a coating of water soluble adherent matrix so that the taggants are easily removed in laundering. Store clerks mark purchased clothing items with a sale confirmation tag of coded nanocrystals by dusting or labeling. Near infrared lamps generally illuminate the store exit area. Mid-infrared detectors, including a photodiode array or camera adapted to the predetermined security and sale confirmation emissions, are located on each side of exit doors.

When a purchased clothing item passes through the exit area, it is illuminated by the near infrared light source to emit both the security label wavelengths and the sale confirmation wavelengths. The emission wavelengths are received by the mid-infrared detectors and communicated as emissions patterns to a computer which interprets the presence of the purchased clothing as a non alarm condition. Should an item of clothing without an appropriate sale confirmation tag enter the exit door area, the resultant emissions pattern would be decoded and interpreted by the computer as an alarm condition followed by an audio and/or visual alarm display signal to store employees.

The security system described here can have various configurations depending, e.g., on the prevention or detection priorities of the store management. Security and sales confirmation tags can be visible labels or essentially invisible dustings. Light source and detection equipment can be intimidating with warning signs or concealed in innocuous fixtures.

Medical Imaging

Nanocrystal compositions of the invention have distinct advantages in the field of medical imaging. For example, the presence, location, and/or identity of medical devices or medical imaging compositions can be determined without the use of hazardous radiation.

Affinity molecules can be linked to nanocrystal taggants, for example, to provide detection and location of specific ligands associated with medical conditions. In a typical example, nanocrystals are attached to antibodies using linker chemistries and injected into a patient to locate pathological tissues. Nanocrystals, excitable in the mid IR spectrum and emitting in the far IR spectrum, are linked to antibodies against cancer specific antigens (such as the HER2 antigen of breast cancer cells) and injected into body fluids of a patient. The presence and location of cancer cells with the antigen can be detected through healthy tissues.

In one example, a monoclonal HER2 antibody is linked to nanocrystals excitable in the mid IR spectrum and emitting in the far IR spectrum with a high intensely (and/or encoded with a unique signature). After injection into a patent with HER2 positive breast cancer, breast tissue is illuminated from one side with a strong general illumination of mid IR light. The breast tissue is viewed from the other side using a camera with a charge coupled device (CCD) matrix light sensor filtered to receive only far IR light. An image is communicated to an analog or digital viewing device where the presence and location of suspected cancer cells can be observed by a medical professional.

Optionally, a cocktail of several different cancer specific antibodies can be linked to nanocrystals encoded with a different signature to provide a medical diagnostic. After a particular antibody localizes at a tissue site, medical technicians can decode the signal at the site to determine what type of cancer cells are present.

Analytical Systems

Nanocrystal taggants can be incorporated into analytical samples for monitoring of processes. Nanocrystals can act as solid supports in certain molecular library synthesis schemes, in which case the nanocrystals can also act as identifying markers in later processing steps. Nanocrystal subsets can be added to reaction vessels to record a reaction history in certain split and pool molecular library syntheses. Nanocrystal taggants can simply be added to molecular library samples to trace their path through analytical systems, such as microfluidic devices. Nanocrystals are incorporated into samples by these and other means they can provide information on the presence, identity, and/or location of the sample in an analytical system.

In one example, the sample is a member of a split and pool synthetic molecular library wherein every sample has a unique combination of introduced nanocrystal subsets. Not only is the synthetic process history embedded in the nanocrystal combination but the identity of the sample can be read before it is removed from the library for analysis. The identified sample is aspirated to the flow channels of a microfluidic chip where the introduction of samples into analytical media is monitored. The identity of each introduced sample is noted and associated with the analytical result. Samples with interesting analytical results can be located for retesting by scanning the array for the associated emissions code.

Light source and detection hardware are configured to monitor samples flowing in channels of the analytical device. The point of sample application is generally illuminated with light of the appropriate excitation wavelengths through an optic system of filters apertures, mirrors and lenses. A detector, including a sensor sensitive to the desired emissions wavelengths, receives light from the point of sample application through an optical fiber. As each sample enters the channel of analytical media, the associated population of nanocrystals is excited by the light source then detected and identified by a quick scan of the emissions wavelengths. The next set of analytical results is assigned to the identified sample. In some applications, photobleaching or sample degradation can be reduced by excitation at IR wavelengths. In other applications, resolution of location determination can be enhanced by excitation at UV wavelengths.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, the methods, compositions and systems described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of encoding and authenticating a nanocrystal spectral code, the method comprising:
   providing a composition comprising a population of nanocrystals that emit light when excited, the population comprising two or more different subsets of nanocrystals wherein each subset comprises a plurality of quantum dots of the same size and/or the same composition;
   determining one or more optical properties of the composition when excited with one or more select excitation wavelengths to encode a unique spectral code for the composition, the unique spectral code comprising at least one optical property defined by the interaction of optical properties of at least two of the two or more different subsets of nanocrystals, wherein the interaction comprises an interaction between the emission frequency of at least the first said subset and the emission frequency of at least the second said subset;
   tagging at least a first object with the composition;
   exciting the first object and/or a second tagged object with the one or more select excitation wavelengths;
   detecting emission wavelengths emitted from the composition of nanocrystals on the first and/or second tagged object; and
   determining whether the first or second tagged object has the unique spectral code;
   wherein said step of determining one or more optical properties occurs before said tagging step, and said tagging step occurs before said step of determining whether the object is tagged with the spectral code.

2. The method of claim 1, wherein the select excitation wavelength comprises light having a wavelength in the visible light spectrum.

3. The method of claim 1, wherein the select excitation wavelength comprises light having a wavelength in the invisible light spectrum.

4. The method of claim 3, wherein the invisible light spectrum is ultraviolet light.

5. The method of claim 3, wherein the invisible light spectrum is near infrared light.

6. The method of claim 3, wherein the invisible light spectrum is infrared light.

7. The method of claim 1, wherein the unique spectral code further comprises one or more excitation and/or emission polarization angles.

8. The method of claim 1, wherein the interaction is between the intensity of at least the first nanocrystal subset and the intensity of at least the second nanocrystal subset.

9. The method of claim 1, further comprising providing the spectral code to an authorized person while not providing an unauthorized person access to the spectral code.

10. The method of claim 1, wherein the one or more excitation wavelengths comprise a combination of two or more different excitation wavelengths, wherein the two or more different excitation wavelengths are generated from one or more narrow-spectrum excitation sources.

11. The method of claim 10, wherein the two or more excitation wavelengths are monochromatic and supplied by one or more narrow spectrum excitation sources.

12. The method of claim 1, wherein said determining whether the first or second tagged object has the unique spectral code comprises:
   determining whether the combination of the one or more excitation wavelengths and the one or more optical properties detected from the object is distinguishable from the determined unique spectral code of the nanocrystal composition.

13. The method of claim 1, wherein the first object is a solid material object selected from the group consisting of: retail items; manufactured goods other than molecules, biomolecules, chemical elements, and chemical compounds; animals, grains, powders, and vehicles.

14. The method of claim 1, wherein two or more excitation wavelengths are selected and used in combination and the population of nanocrystals is excited with the two or more excitation wavelengths simultaneously.

15. The method of claim 14, wherein the two or more excitation wavelengths are generated from separate narrow-spectrum excitation sources.

16. The method of claim 1, wherein the unique spectral code is stored in a computer.

17. The method of claim 1, wherein said tagging is other than applying a dopant to a nanocrystal.

18. The method of claim 1, further comprising withholding access to the unique spectral code by unauthorized persons.

19. The method of claim 1, wherein the one or more optical properties comprises one or more of the following: excitation wavelength, excitation polarization angle, emission frequency, emission shape, emission polarization angle, emission intensity, and emission spectral width.

20. The method of claim 1, wherein the interaction is between the emission wavelength of at least the first nanocrystal subset and the excitation wavelength of at least the second nanocrystal subset, wherein the interaction causes the emission of at least the first nanocrystal subset to excite at least the second nanocrystal subset.

21. A method of encoding and authenticating a nanocrystal spectral code, the method comprising:
   providing a composition comprising a population of nanocrystals that emit light when excited, the population comprising two or more different subsets of nanocrystals wherein each subset comprises a plurality of quantum dots of the same size and/or the same composition;
   determining one or more optical properties of the composition when excited with one or more select excitation wavelengths to encode a unique spectral code for the composition, the unique spectral code comprising a first emission wavelength of a first nanocrystal subset and a second emission wavelength of a second nanocrystal subset, wherein the first and second emission wavelengths are the same;

tagging at least a first object with the composition;

exciting the first object and/or a second tagged object with the one or more select excitation wavelengths;

detecting one or more emission wavelengths and the corresponding emission intensity of light emitted from the composition of nanocrystals on the first and/or second tagged object; and determining whether the first and/or second tagged object has the unique spectral code;

wherein said step of determining one or more optical properties occurs before said tagging step, and said tagging step occurs before said step of determining whether the object is tagged with the spectral code.

\* \* \* \* \*

UNITED STATES PATENT AND TRADEMARK OFFICE
CERTIFICATE OF CORRECTION

| | | |
|---|---|---|
| PATENT NO. | : 7,912,653 B1 | Page 1 of 1 |
| APPLICATION NO. | : 11/075364 | |
| DATED | : March 22, 2011 | |
| INVENTOR(S) | : Scher et al. | |

It is certified that error appears in the above-identified patent and that said Letters Patent is hereby corrected as shown below:

On the Title Page:

In item (63), after "Continuation", please insert -- -in-Part --.

Signed and Sealed this
Tenth Day of May, 2011

David J. Kappos
*Director of the United States Patent and Trademark Office*